United States Patent
Zhu et al.

(10) Patent No.: US 10,435,424 B2
(45) Date of Patent: Oct. 8, 2019

(54) CYTOTOXIC PLATINUM COMPLEX, ITS PREPARATION AND THERAPEUTIC USE

(71) Applicant: City University of Hong Kong, Kowloon (HK)

(72) Inventors: Guangyu Zhu, Mid-Level West (HK); Lili Ma, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 8 days.

(21) Appl. No.: 15/371,532

(22) Filed: Dec. 7, 2016

(65) Prior Publication Data
US 2018/0155382 A1     Jun. 7, 2018

(51) Int. Cl.
*C07F 15/00* (2006.01)

(52) U.S. Cl.
CPC ................ *C07F 15/0093* (2013.01)

(58) Field of Classification Search
CPC ..................................................... C07F 15/00
See application file for complete search history.

(56) References Cited

PUBLICATIONS

Ang et al., 2005, caplus an 2005:31552.*
Ma et al., Chemical Communications, 2015, 51(29), 6301-6304.*

* cited by examiner

*Primary Examiner* — Sun Jae Yoo
(74) *Attorney, Agent, or Firm* — Renner Kenner Greive Bobak Taylor & Weber

(57) ABSTRACT

Platinum(IV) complexes especially suitable for antitumor therapy and methods for their preparation. Further provided is a method for treating a subject, in particular a human, suffering from a disease comprising administering a platinum(IV) complex of the present invention, which disease is especially preferably but not exclusively a cancer. Further provided is a method of inhibiting the growth of tumor cells by contacting the cells with a platinum(IV) complex of the present invention and a pharmaceutical composition comprising a platinum(IV) complex of the present invention. The platinum(IV) complexes of the present invention represent a novel class of platinum anticancer prodrugs for the treatment of diseases especially of cancer. The platinum(IV) complexes of the present invention exhibit advantageously high cytotoxic activity in various cancer types superior to commonly used platinum-based complexes. In addition, the complexes proved to be highly effective even against cisplatin-resistant cancers.

18 Claims, 3 Drawing Sheets

CYTOTOXIC PLATINUM COMPLEX, ITS PREPARATION AND THERAPEUTIC USE

TECHNICAL FIELD

The present invention relates to a novel platinum(IV) complex especially suitable for antitumor therapy and a method for preparing it. Further provided is a method for treating a subject, in particular a human, suffering from a disease comprising administering the platinum(IV) complex of the present invention. Said disease is especially preferably but not exclusively a cancer. Further provided is a method of inhibiting the growth of tumor cells by contacting the cells with the platinum(IV) complex of the present invention and a pharmaceutical composition comprising said platinum complex.

BACKGROUND OF THE INVENTION

Cancer remains a life-threatening disease affecting a steadily increasing number of people overall in the world. Platinum-based chemotherapeutic compounds, including cisplatin, carboplatin and oxaliplatin, have been widely applied for the treatment of different types of cancer in clinical trials for decades. These platinum complexes react in vivo, and they are proposed to bind to DNA and subsequently to cause crosslinking of DNA, which ultimately triggers apoptosis.

Although over 50% of cancer patients have been treated with platinum-based chemotherapeutic compounds, these compounds are associated with severe side effects. In addition, both intrinsic and acquired resistances against these compounds have been observed after the treatment with these compounds which further significantly limits their clinical use.

Thus, there remains a strong need for new and effective compounds suitable for treating cancer with acceptable side effects that can be used either as alternatives or alternatively in addition to common chemotherapeutic compounds such as cisplatin or other anticancer therapies such as radiotherapy and which are effective even if the cancer is or has developed chemoresistance against commonly used chemotherapeutic compounds such as cisplatin.

SUMMARY OF THE INVENTION

The first aspect of the present invention relates to a platinum(IV) complex. Said platinum complex comprises a structure of Formula (I):

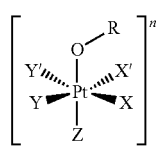

Formula (I)

X, X', Y, Y' and Z are independently selected from an electron donor ligand and may be linked to each other in any combination.

n is selected from zero, any positive charge or any negative charge.

R is an aryl-comprising moiety selected from the group consisting of

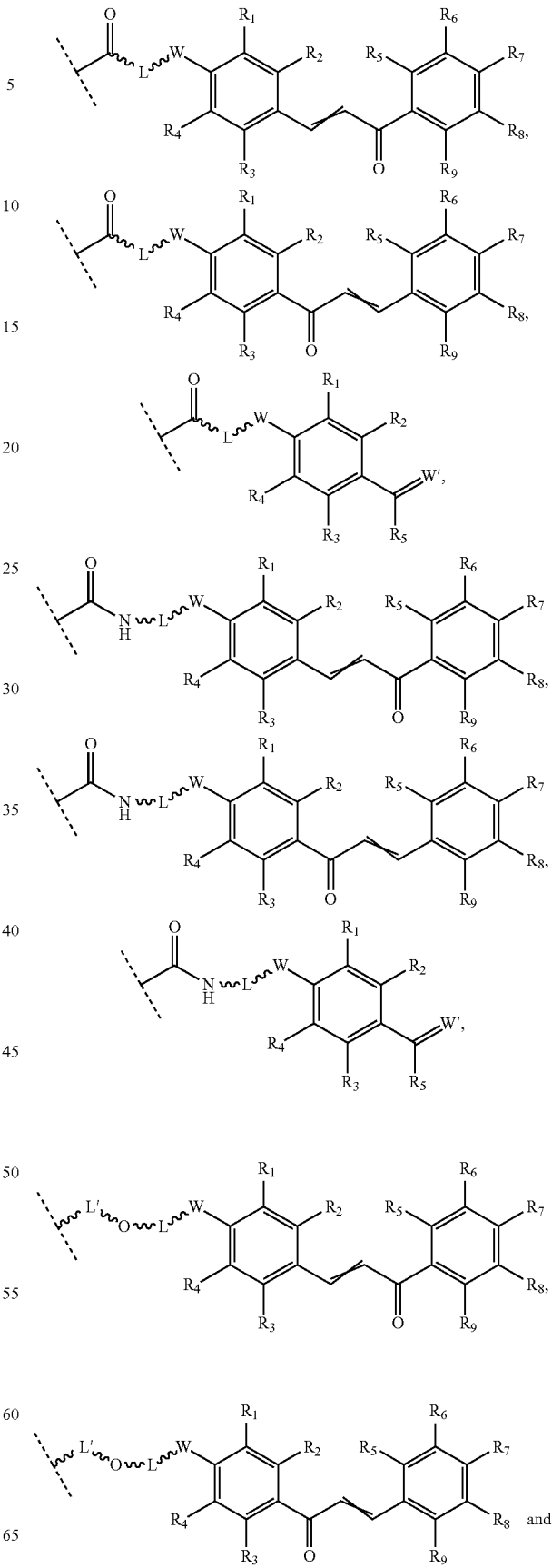

-continued

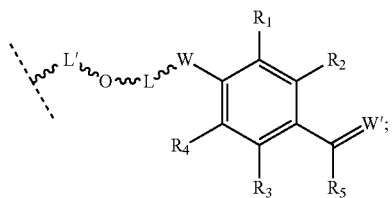

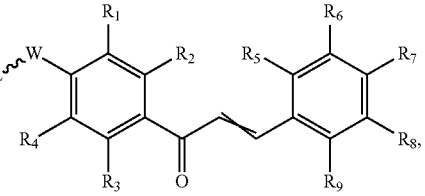

with L and L' being a linker group, W being a linker atom, W' being an atom or group which can be attached by a double bond and $R_1$ to $R_9$ being independently selected from a substituent or a hydrogen atom. ≈≈≈ as used in this invention means a double bond and indicates that the configuration might be the (E) and (Z) configuration, i.e. it covers the (E) and the (Z) configuration.

The platinum(IV) complex of the present invention comprises a structure of Formula (I) with the provision that the platinum complex is not chalcoplatin.

Further provided with the present invention is a method for preparing the platinum(IV) complex described above, i.e. for preparing a platinum complex comprising a structure of Formula (I):

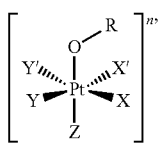

Formula (I)

with X, X', Y, Y', Z, n and R as defined above.

Said method comprises linking a platinum complex precursor comprising a structure of Formula (XI):

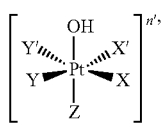

Formula (XI)

which is in particular a platinum(IV) complex precursor with an aryl-comprising moiety R to form the platinum(IV) complex as described above, wherein X, X', Y, Y' and Z are as defined above, n' means zero or any positive or negative charge and wherein R is an aryl-comprising moiety selected from one of:

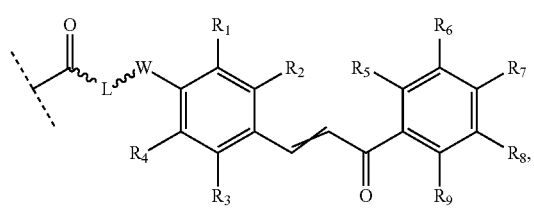

with L, L', W, W' and $R_1$ to $R_9$ as defined above.

The present invention in a third aspect refers to a method for treating a subject such as a human suffering from a disease such as a tumor, in particular a cancer, comprising administering an effective amount of a platinum(IV) complex as described above to said subject, i.e. comprising administering a platinum(IV) complex comprising a structure of Formula (I) to said subject:

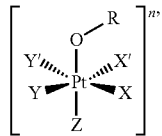

Formula (I)

with X, X', Y, Y', Z, n and R as defined above and with the provision that the platinum complex is not chalcoplatin.

The present invention further provides a pharmaceutical composition comprising:
(i) a platinum(IV) complex as described above; and
(ii) a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof.

According to the invention is also the platinum(IV) complex described above for use as a medicament for the treatment of cancer. The platinum(IV) complex can be used in an effective amount for treating a living organism like an animal or a human, in particular a mammal, preferably a human. Another aspect of the invention refers to the use of the platinum(IV) complex described above for preparing a medicament for treatment of cancer. The platinum(IV) complex described above may be used in monotherapy or in combination with at least a further chemotherapeutic compound.

In another aspect, the invention provides a method of inhibiting the growth of tumor cells. Said method comprises the step of contacting a population of tumor cells such as a population of cancer cells with the platinum(IV) complex described above. In particular, the cell growth is reduced and/or cell death is induced.

The platinum(IV) complex of the present invention represents a novel class of platinum anticancer prodrugs for the treatment of diseases especially cancer. In particular, the inventors could show that the platinum(IV) complexes of the present invention can have advantageously high cytotoxic activity against cancer cells, with the platinum(IV) complex of Formula (IIa) being among the most active platinum(IV) prodrugs known so far. For example, the inventor found that said platinum(IV) complex is significantly more active than both cisplatin and chalcoplatin, and the $IC_{50}$ values of said complex are in the nanomolar range in cells from several cancer types. In addition, the complexes proved to be highly effective against cisplatin-resistant cancer cells. For example, the platinum(IV) complex of Formula (IIa) proved to be able to overcome cisplatin resistance with reduced Resistant Factors compared to cisplatin.

Therefore, compared with the existing and commonly used platinum-based chemotherapeutic compound cisplatin, the platinum(IV) complexes of the present invention have the advantage of superior effectiveness, especially against cisplatin-resistant cancer cells and, thus, represent a highly promising treatment option such as for cancer therapy.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and drawing.

DETAILED DESCRIPTION OF THE INVENTION

Figure 1:
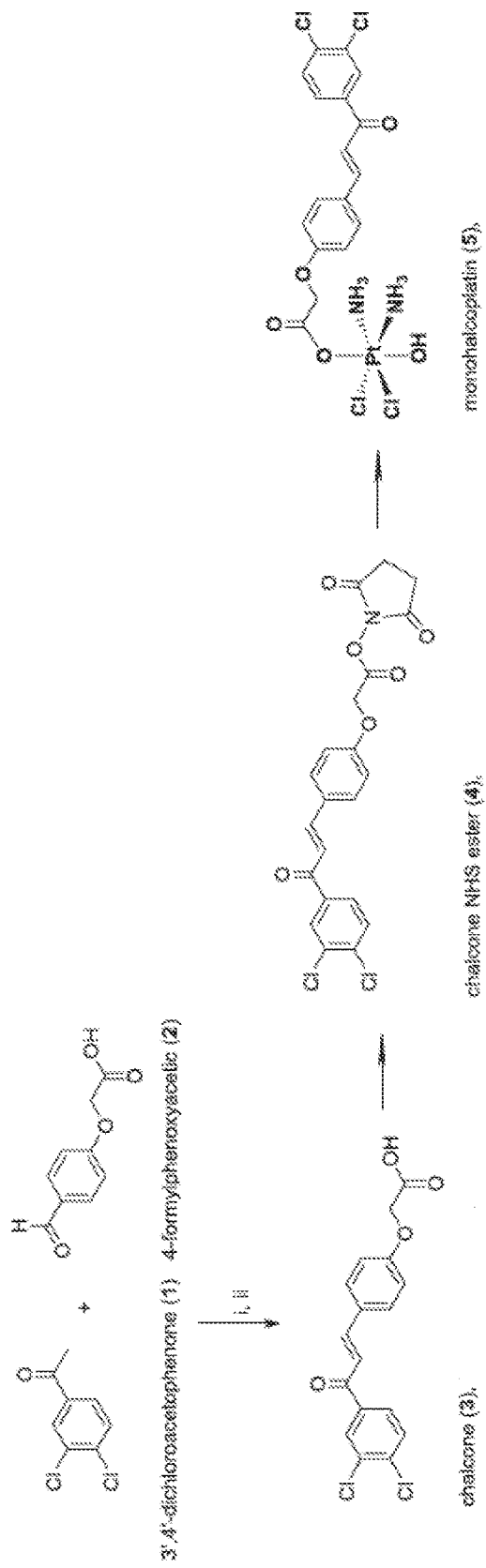
FIG. 1 summarizes the synthesis route of monochalcoPt (IV)

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

Other than in the working examples, or where otherwise indicated, all numbers used herein should be understood as modified in all instances by the term "about" The term "about" when used in connection with a number can mean, for example, ±2%.

Moreover, the words "example" or "exemplary" used in this invention are intended to serve as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

The present invention provides a platinum(IV) complex. Said platinum(IV) complex comprises a structure of Formula (I):

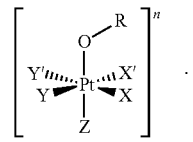

Formula (I)

Where X, X', Y, Y' and Z are independently selected from an electron donor ligand and may be linked to each other in any combination.

n is selected from zero, any positive charge or any negative charge.

R is an aryl-comprising moiety selected from the group consisting of:

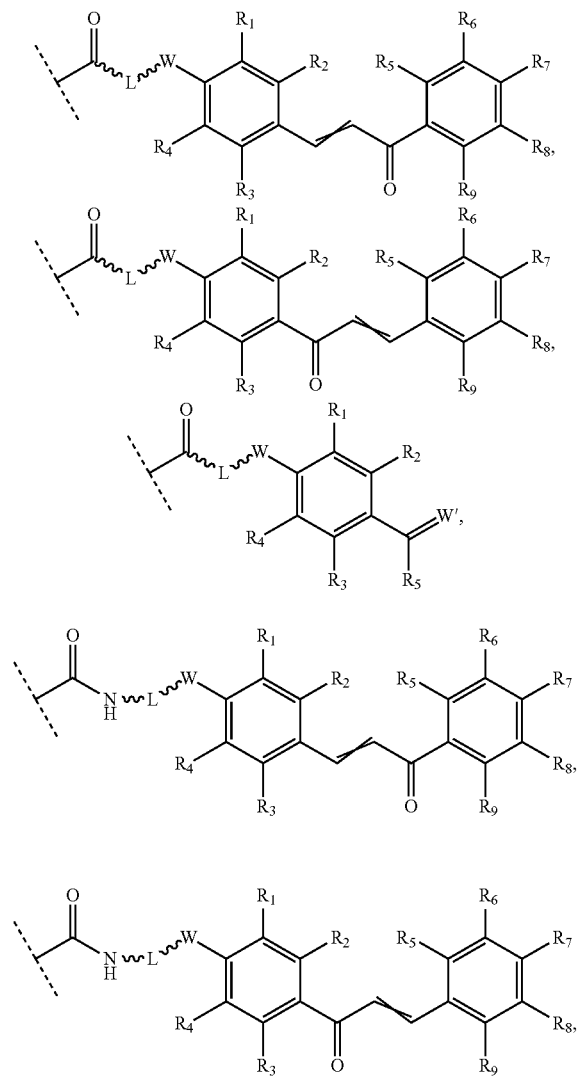

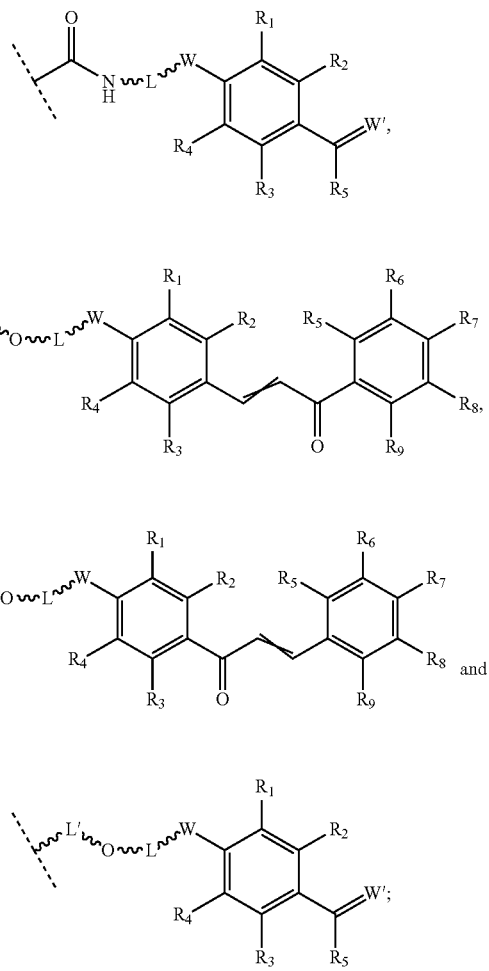

with L and L' being a linker group, W being a linker atom, W' being an atom or group which can be attached by a double bond, $R_1$ to $R_9$ being independently selected from a substituent or a hydrogen atom, and ⁓ is a double bond covering the (E) and (Z) configuration.

The platinum(IV) complex of the present invention comprises a structure of Formula (I) with the provision that the platinum complex is not chalcoplatin, i.e. with the proviso that the platinum(IV) complex does not have the following structure:

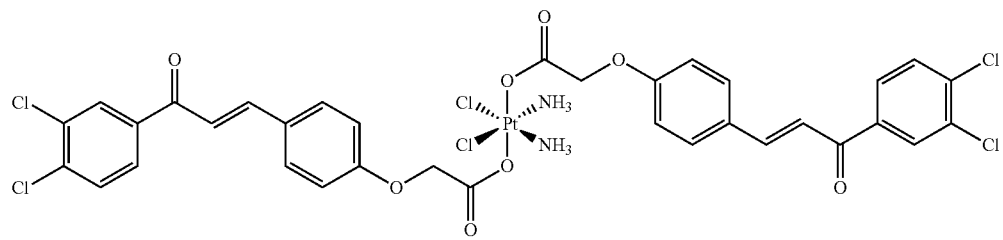

I.e. with the proviso that when R is

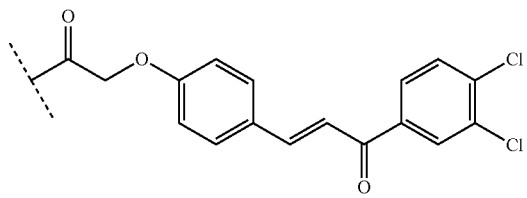

and either the ligands Y and Y' are amine (NH$_3$, i.e. amine (NH$_3$) as ligand) each and X and X' are chlorido each or if Y and Y' are chlorido each and X and X' are amine (NH$_3$) each, Z is not —OR.

Said platinum(IV) complex can be present in form of a salt, i.e. suitable counterions may be present or in form of a solvate. A counterion might affect the solubility or other chemical or physical properties of the platinum(IV) complex, wherein the exact nature of the counterion is not critical. The counterion is preferably pharmaceutically acceptable, i.e. not with therapeutically relevant toxicity in the amounts used. Counterions can in particular be anions which are unlikely to bind directly to the platinum center, i.e. non-coordinating anions. As used herein, the term "solvate" refers to a complex of variable stoichiometry formed by a solute, i.e. the platinum(IV) complex, and a solvent. If the solvent is water, the solvate formed is a hydrate.

The platinum in the platinum complex of the present invention is in the oxidation state (IV), i.e. the platinum complex of the present invention is a platinum(IV) complex.

R is an aryl-comprising moiety. The term "aryl" as used herein, refers to an aromatic monocyclic ring system having 6 ring atoms, of which all the ring atoms are carbon, and which ring may be substituted with $R_1$ to $R_9$. R comprises one or two aryl rings. Said part of R is also referenced as the "aromatic part". "Aromatic" means the presence of a delocalized, conjugated π-electron system.

R further comprises a linker atom W which is an atom directly attached to an aryl and can include, but is not limited to, a heteroatom such as oxygen (O) or sulfur (S). In particular embodiments of the present invention, W is an oxygen atom.

W' can be any atom or a group which can be attached by a double bond provided that this results in the formation of a stable moiety, including, but not limited to, a heteroatom such as an oxygen atom, a sulfur atom or a nitrogen (N) atom or a heteroatom-containing group. In particular embodiments of the present invention, W' is an oxygen atom or a sulfur atom, in particular W' is an oxygen atom.

The linker group L is an organic unit of any lengths comprising atoms or groups to link, i.e. to connect, two parts of the platinum complex of the present invention, namely the 'platinum part' of the platinum complex and the 'aromatic part' of R together, it thus links the platinum part with the W-aromatic part of R. Not limiting examples include a straight chain or branched alkanediyl or alkenediyl chain. In particular embodiments of the present invention, L is —(CH$_2$)$_m$—, wherein m is an integer which is >0 for example m is 1, 2, 3 or 4, most preferably L is —CH$_2$—, i.e. a methanediyl group.

The linker group L' is an organic unit of any lengths comprising atoms or groups to link, i.e. to connect, the two oxygen atoms together. L' can be, for example, a straight chain or branched alkanediyl or alkenediyl chain or a carbon-oxygen chain. In particular embodiments of the present invention, L' is —(CH$_2$)$_{m'}$—i.e. a methanediyl group and m' is an integer and >0 such as 1, 2 or 3, in particular m' is 1.

$R_1$ to $R_9$ are substituents which can be, for example, but not limited to, a nitrogen-containing group, an oxygen-containing group, a phosphorous(P)-containing group, a sulfur-containing group, alkyl groups, a halogen atom or a hydrogen atom or the like. $R_1$ to $R_9$ are in particular embodiments of the present invention selected from a hydrogen atom or a halogen atom, more preferably from a hydrogen atom or a chlorine atom.

An electron donor ligand means a ligand which is electron donating, i.e. has a donor atom with electron-donating ability such as a nitrogen atom, an oxygen atom, a phosphorous (P) atom or a sulfur atom. Non-limiting examples of electron donor ligands are nitrogen-containing ligands, oxygen-containing ligands, phosphorous-containing ligands, sulfur-containing ligands and halogen containing ligands. Electron donor ligands can, for example, include, imine, aqua, halido (i.e. halide ions in particular including chlorido, bromido or fluorido), amines, diamines, triamines, amine (NH$_3$), alkyl, cyanido, nitrato, hydroxido, alkoxy, phenoxy, anions of an alkyl mono- or poly-, such as di-, carboxylic acid such as oxalato or dianions of glycolic acid, an alcoholato ligand, alkylthio, thiolato, phosphito, phosphane, 1-diketone, nitrato, a heterocycle such as pyridine or 2-methylpyridine or it can be —OR with R being an aryl-comprising moiety as defined above. The term "alkyl" as used herein refers to saturated, straight-chain or branched hydrocarbons which may, for example, contain between 1 and 20 carbon atoms such as 1 to 5 carbon atoms. The electron donor ligands in particular include amine (NH$_3$), aqua, halido such as chlorido, hydroxido, oxalato, diamines such as 1,2-cyclohexanediamine or —OR with R being an aryl-comprising moiety as defined above. Y, Y', X, X' and Z may optionally be linked to each other in any combination to form polydentate ligands, in particular bidentate ligands. In particular embodiments, X and X' are linked to each other to form a bidentate ligand and/or Y and Y' are linked to each other to form a bidentate ligand.

In particular embodiments of the present invention, X, X', Y and Y' are independently selected from amine (NH$_3$), aqua, halido such as chlorido, hydroxido, oxalato or diamines such as 1,2-cyclohexanediamine, in particular from amine (NH$_3$), chlorido, hydroxido, oxalato or 1,2-cyclohexanediamine and Z is selected from amine (NH$_3$), aqua, halido such as chlorido, hydroxido, oxalato or diamines such as 1,2-cyclohexanediamine or —OR with R being an aryl-comprising moiety as defined above, in particular Z is selected from amine (NH$_3$), chlorido, hydroxido, oxalato, 1,2-cyclohexanediamine or —OR. 1,2-cyclohexanediamine means in particular trans-(1R,2R)-1,2-cyclohexanediamine.

n is zero or any positive or any negative charge. In embodiments of the present invention n is zero, i.e. the platinum complex is in particular a neutral platinum complex.

I.e., the platinum(IV) complex of the present invention comprises a structure selected from one of Formulas (II) to (X):

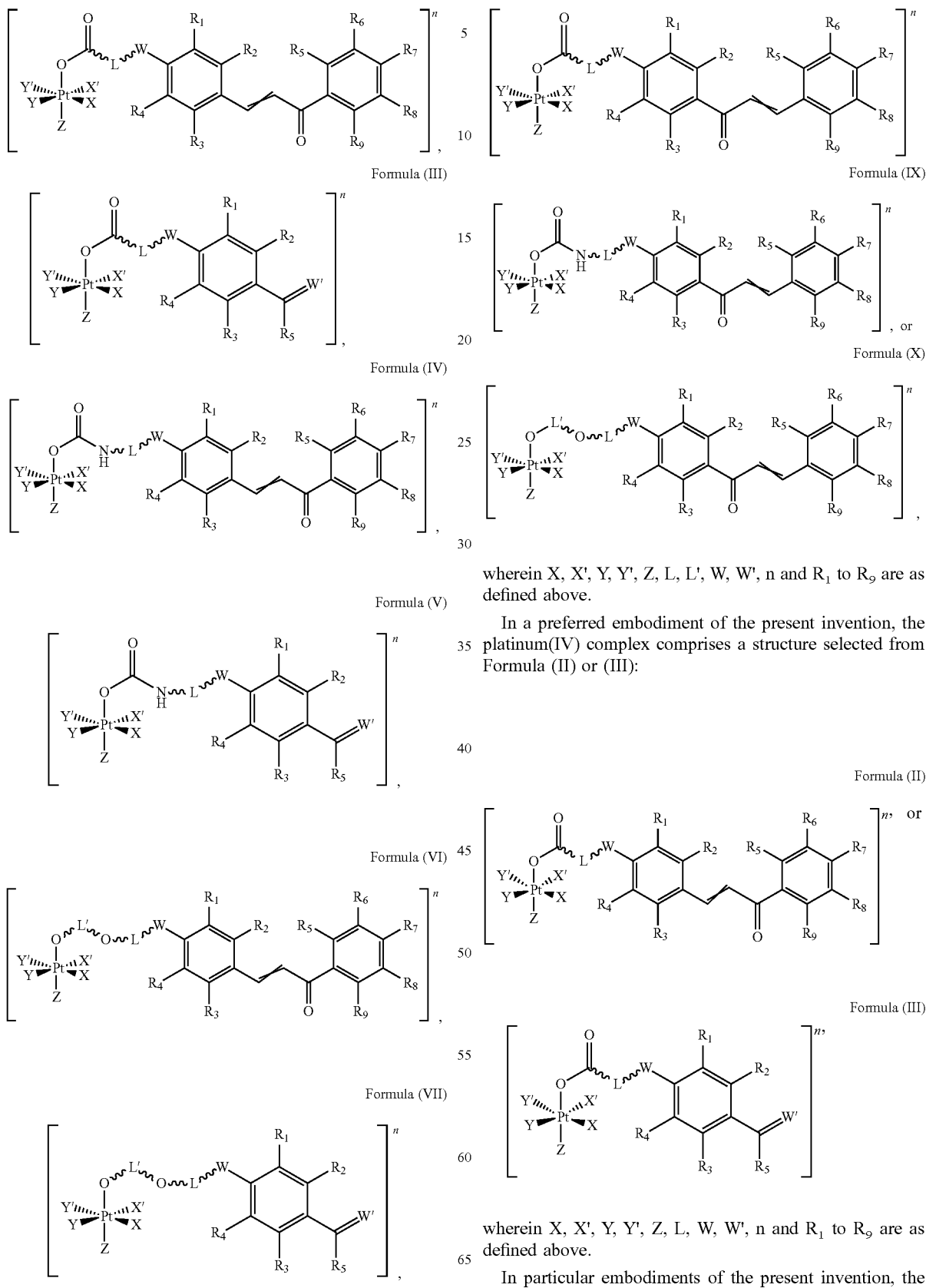
wherein X, X', Y, Y', Z, L, L', W, W', n and $R_1$ to $R_9$ are as defined above.
In a preferred embodiment of the present invention, the platinum(IV) complex comprises a structure selected from Formula (II) or (III):
wherein X, X', Y, Y', Z, L, W, W', n and $R_1$ to $R_9$ are as defined above.
In particular embodiments of the present invention, the platinum(IV) complex comprises a structure of Formula (II):

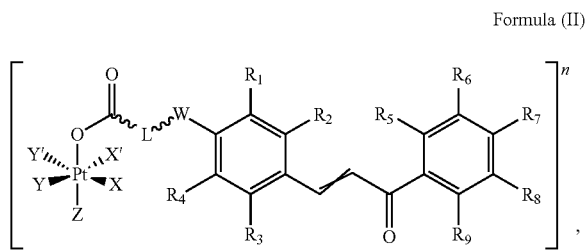

Formula (II)

wherein X, X', Y, Y', Z, L, W, n and $R_1$ to $R_9$ are as defined above. Preferably, X, X', Y and Y' are independently selected from amine ($NH_3$), aqua, halido, hydroxido, oxalato or diamines and Z is selected from amine ($NH_3$), aqua, halido, hydroxido, oxalato or diamines or —OR with R being an aryl-comprising moiety as defined above. Further preferred, X, X', Y and Y' are independently selected from amine ($NH_3$), oxalato, 1,2-cyclohexanediamine and a halido and Z is selected from hydroxido or —OR with R being an aryl-comprising moiety as described above, in particular R is:

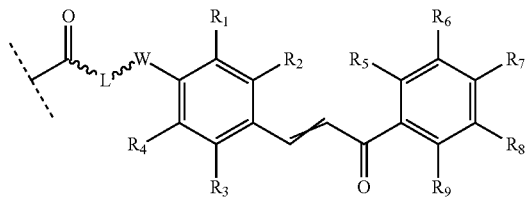

with L, W and $R_1$ to $R_9$ as described within this embodiment, i.e. R in Formula (II) most preferably corresponds to the R in —OR of Z.

L is preferably —$(CH_2)_m$—, wherein m is an integer selected from 1, 2, 3 or 4, more preferably m is 1. W is preferably selected from an oxygen atom or a sulfur atom, more preferably W is an oxygen atom. $R_1$ to $R_9$ are preferably independently selected from a hydrogen atom or a halogen atom, more preferably $R_1$ to $R_4$ are hydrogen atoms and $R_5$ to $R_9$ are independently selected from a hydrogen atom or a halogen atom with most preferably $R_7$ and $R_8$ being a chloride atom each and $R_5$, $R_6$ and $R_9$ being a hydrogen atom each.

Most preferably, the platinum(IV) complex in such embodiments comprises a structure of Formula (IIa) or (IIb) and in particular essentially consists of a compound of Formula (IIa) or (IIb):

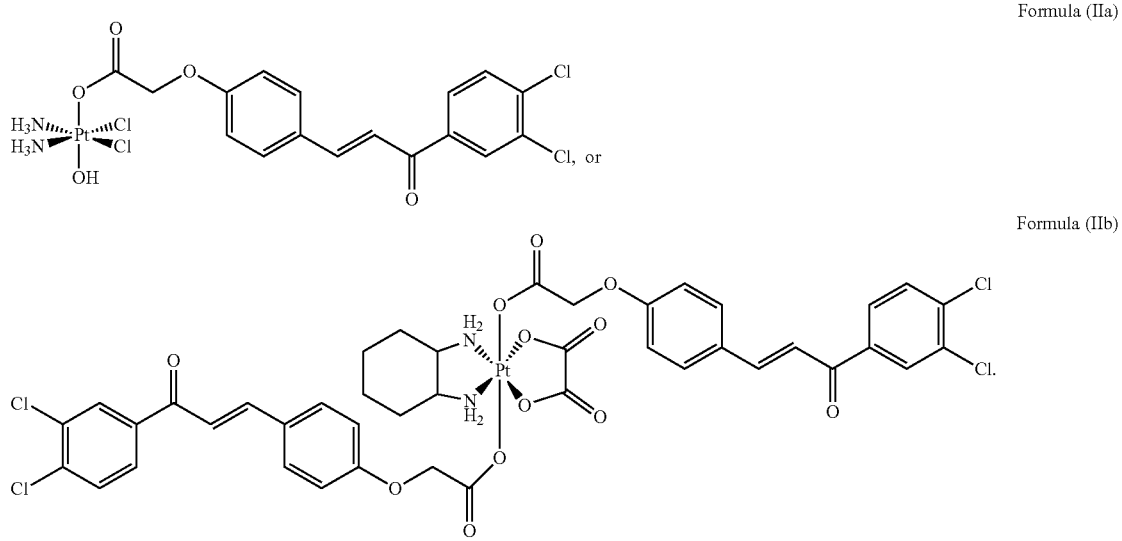

Formula (IIa)

Formula (IIb)

In alternative preferred embodiments of the present invention, the platinum(IV) complex comprises a structure of Formula (III):

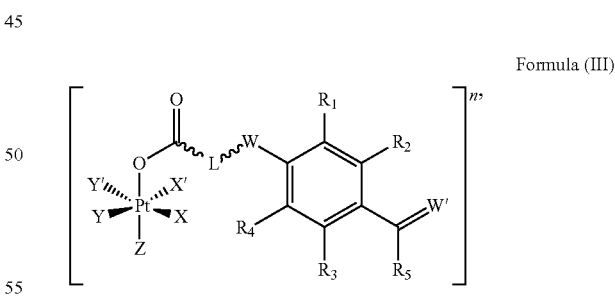

Formula (III)

wherein X, X', Y, Y', Z, L, W, W', n and $R_1$ to $R_5$ are as defined above. Preferably, X, X', Y and Y' are independently selected from amine ($NH_3$), aqua, halido, hydroxido, oxalato or diamines and Z is selected from amine ($NH_3$), aqua, halido, hydroxido, oxalato or diamines such as 1,2-cyclohexanediamine or —OR with R being an aryl-comprising moiety as described above. Further preferred, X, X', Y and Y' are independently selected from amine ($NH_3$), a halido, oxalato and 1,2-cyclohexanediamine and Z is selected from hydroxido or —OR with R being an aryl-comprising moiety as described above, in particular R is:

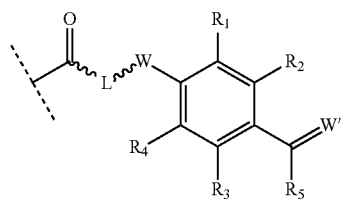

with L, W, W' and $R_1$ to $R_5$ as described within this embodiment, i.e. R in Formula (III) most preferably corresponds to the R in —OR of Z.

L is preferably —$(CH_2)_m$—, wherein m is an integer selected from 1, 2, 3 or 4, more preferably m is 1. W is preferably selected from an oxygen atom or a sulfur atom, more preferably W is an oxygen atom. W' is preferably an oxygen atom. $R_1$ to $R_4$ are preferably independently selected from a hydrogen atom or a halogen atom and $R_5$ is a hydrogen atom, more preferably all of $R_1$ to $R_5$ are hydrogen atoms.

Most preferably, the platinum complex in such embodiments comprises a structure of Formula (IIIa), (IIIb) or (IIIc) and in particular essentially consists of a compound of Formula (IIIa), (IIIb) or (IIIc):

Formula (IIIa)

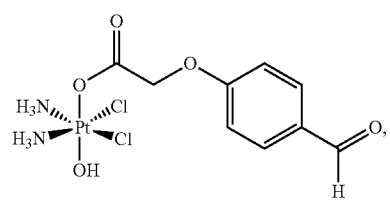

Formula (IIIb)

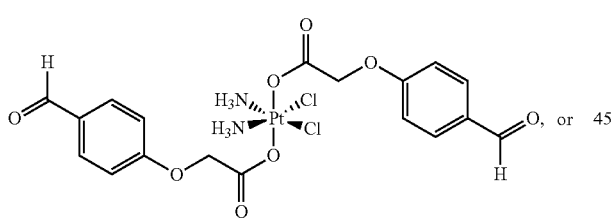

or

Formula (IIIc)

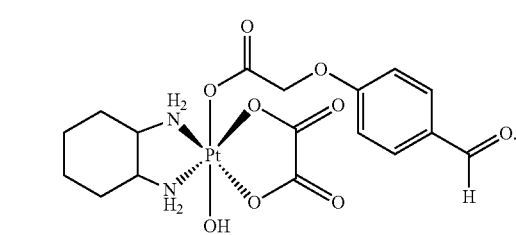

Further provided with the present invention is a method for preparing the platinum(IV) complex described above, i.e. for preparing a platinum(IV) complex comprising a structure of Formula (I):

Formula (I)

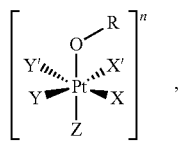

with X, X', Y, Y' and Z, n and R as defined above.

Said method comprises linking a platinum complex precursor which is in particular a platinum(IV) complex precursor and which comprises a structure of Formula (XI):

Formula (XI)

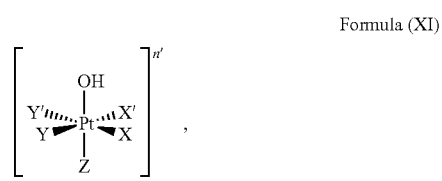

with an aryl-comprising moiety R to form the platinum(IV) complex as described above, wherein X, X', Y, Y' and Z are as defined above, n' means zero or any positive or negative charge and wherein R is selected from one of:

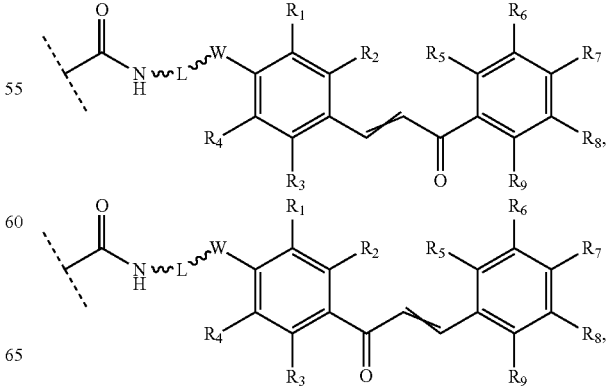

-continued

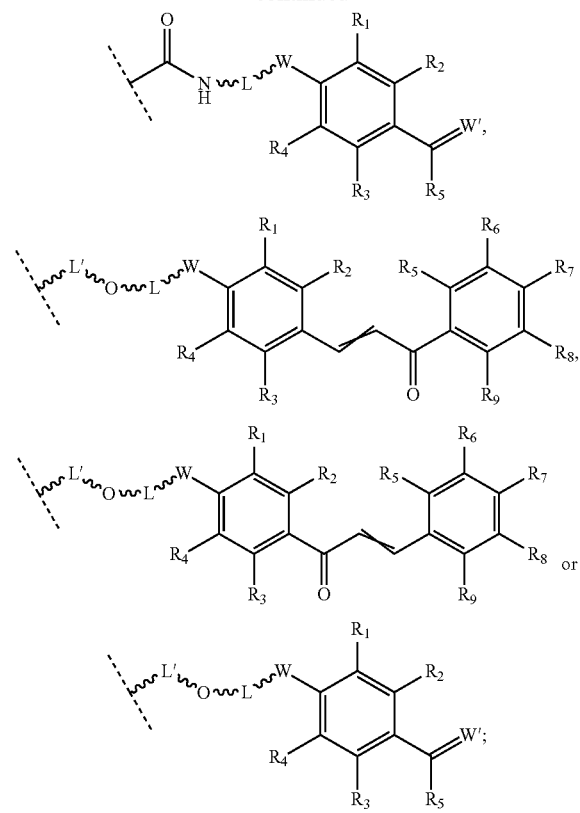

wherein L, L', W, W' and $R_1$ to $R_9$ are as defined above.

The platinum complex precursor in particular platinum (IV) complex precursor can comprise a structure of Formula (XIa):

Formula (XIa)

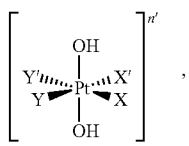

i.e. Z is hydroxido. Particular platinum complex precursors comprise a structure of Formula (XIb) or (XIc) given further below and are in particular platinum(IV) precursor complexes, i.e. most preferably the platinum complex precursor is a platinum(IV) complex precursor selected from a structure of Formula (XIb) or (XIc) given further below. The method is preferably carried out under inert atmosphere such as under argon.

In an embodiment of the present invention, the method is for preparing a platinum(IV) complex comprising a structure of Formula (II) such as of Formula (IIa) or (IIb) comprising linking a platinum complex precursor of Formula (XI) such as of Formula (XIa) with an aryl-comprising moiety which is

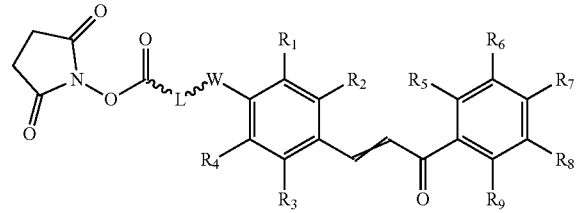

which method comprises steps of:
(i) optionally preparing a hydroxysuccinimide(NHS)-ester of Formula (XII) such as of Formula (XIIa);
(ii) reacting a platinum complex precursor of Formula (XI) such as of Formula (XIa) with the N-hydroxysuccinimide(NHS)-ester of Formula (XII) such as of Formula (XIIa):

Formula (XII)

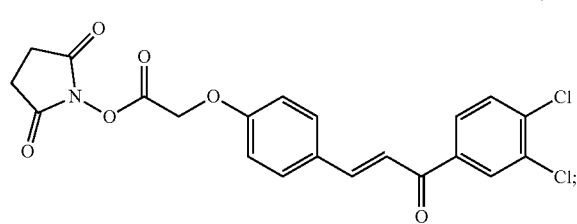

with L, W and $R_1$ to $R_9$ as defined above, such as

Formula (XIIa)

(iii) isolating the platinum(IV) complex of Formula (II) such as of Formula (IIa) or (IIb).

Step (ii) in particular comprises:
a) preparing a mixture of the platinum complex precursor and the NHS-ester in a reaction solvent;
b) stirring the mixture after step a) for at least about 8 h at a temperature of at least about 20° C.

"Isolating" the platinum(IV) complex means at least partially separating the platinum(IV) complex from other components such as side products, the reactants and the solvent present in the reaction mixture after step (ii). Step (iii) in particular comprises filtering the mixture for obtaining a filtrate, adding a precipitation solvent to the filtrate for obtaining a precipitate and washing the precipitate with a washing solvent.

The reaction solvent in step a) is preferably dimethyl sulfoxide (DMSO). In particular, the NHS-ester is added in step a) in form of a mixture with at least a part of the reaction solvent, in particular DMSO. The precipitation solvent can be a halogenated hydrocarbon and/or a dialkyl ether, in particular dichloromethane, diethyl ether or a mixture of both. The washing solvent can be a halogenated hydrocarbon, in particular dichloromethane.

In another embodiment of the method of the present invention, the method is for preparing a platinum(IV) complex comprising a structure of Formula (III) such as of Formula (IIIa), (IIIb) or (IIIc) comprising linking a platinum complex precursor of Formula (XI) such as of Formula (XIa) with an aryl-comprising moiety which is

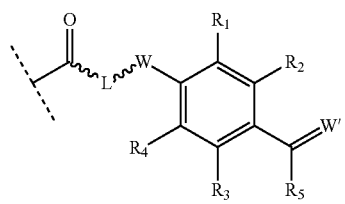

which method comprises steps of:
(i) optionally preparing a hydroxysuccinimide(NHS)-ester of Formula (XIII) such as of Formula (XIIIa);
(ii) reacting a platinum complex precursor of Formula (XI) such as of Formula (XIa) with the NHS-ester of Formula (XIII) such as of Formula (XIIIa):

Formula (XIII)

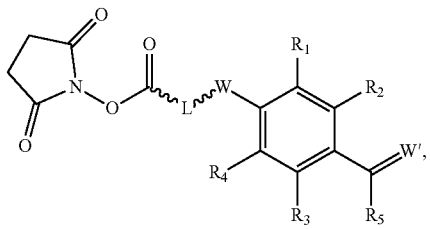

with L, W, W' and $R_1$ to $R_5$ as defined above, such as

Formula (XIIIa)

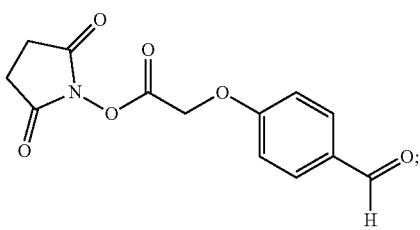

and
(iii) isolating the platinum(IV) complex of Formula (III) such as of Formula (IIIa), (IIIb) or (IIIc).

Step (ii) in particular comprises:
a) preparing a mixture of the platinum complex precursor and the NHS-ester in a reaction solvent;
b) stirring the mixture after step a) for at least about 8 h at a temperature of at least about 20° C.

Step (iii) in particular comprises filtering the mixture for obtaining a filtrate, adding a precipitation solvent to the filtrate for obtaining a precipitate and washing the precipitate with a washing solvent.

The reaction solvent in step a) is preferably dimethyl sulfoxide (DMSO). In particular, the NHS-ester is added in step a) in form of a mixture with at least a part of the reaction solvent, in particular DMSO. The precipitation solvent can be a halogenated hydrocarbon and/or a dialkyl ether, in particular dichloromethane, diethyl ether or a mixture of both. The washing solvent can be a halogenated hydrocarbon, in particular dichloromethane.

The methods may optionally comprise the step (i) of preparing the NHS-ester. The NHS-ester of Formula (XII) such as of Formula (XIIa) or of Formula (XIII) such as of Formula (XIIIa) may be prepared comprising steps of:
a) providing a mixture of a compound of Formula (XIV) such as (XIVa) or (XV) such as (XVa) and 1-ethyl-3-(3-dimethylaminopropyl)-carbodiimide (EDC) and N-hydroxysuccinimide (NHS):

Formula (XIV)

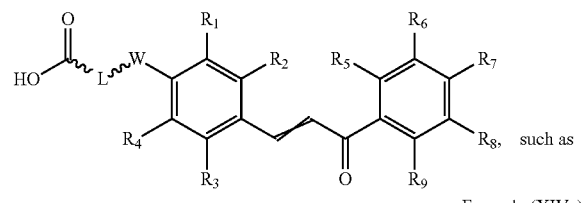

such as

Formula (XIVa)

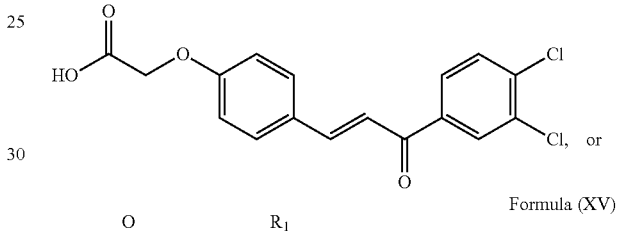

Cl, or

Formula (XV)

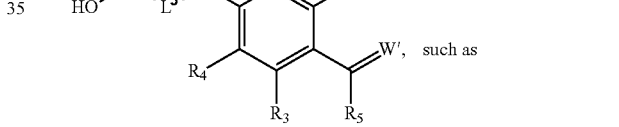

such as

Formula (XVa)

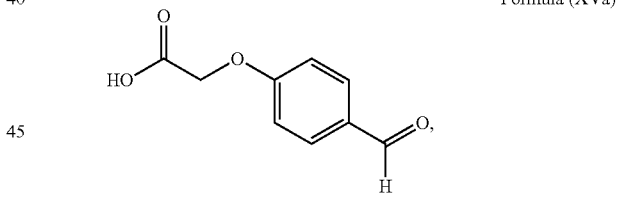

with L, W, W' and $R_1$ to $R_9$ as defined above;
b) isolating the NHS-ester.

Step a) is preferably carried out by stirring the mixture in a reaction solvent at a temperature between about 20° C. and about 30° C., such as at about 25±2° C., for at least about 8 h, in particular for at least about 10 h. The reaction solvent in this step a) is preferably an organic nitrile, in particular acetonitrile.

"Isolating" the NHS-ester in step b) means at least partially separating the NHS-ester from other components such as side products, the reactants and the solvent present in the reaction mixture after step a). Step b) in particular comprises filtering the mixture for obtaining a residue and washing the residue with water and optionally freeze-drying the residue.

In a particular embodiment, the method is for preparing a platinum complex of Formula (IIa) and the method comprises steps of:

(i) optionally preparing an N-hydroxysuccinimide(NHS)-ester of Formula (XIIa):

Formula (XIIa)

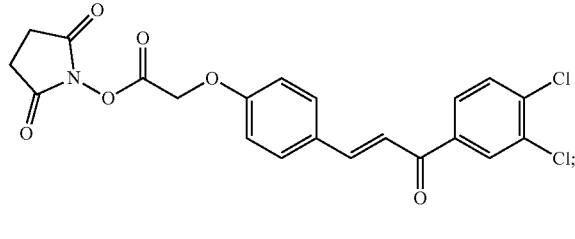

comprising:
a) providing a mixture of a compound of Formula (XIVa) and 1-ethyl-3-(3-dimethylaminopropyl)-carbodiimide (EDC) and N-hydroxysuccinimide (NHS):

Formula (XIVa)

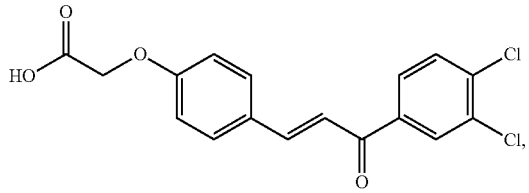

and stirring the mixture in a reaction solvent such as acetonitrile at a temperature between about 20° C. and about 30° C., such as at about 25±2° C., for at least about 8 h, in particular for at least about 10 h;
b) isolating the NHS-ester in particular comprising filtering the mixture for obtaining a residue and washing the residue with water and optionally freeze-drying the residue;
(ii) reacting a platinum complex precursor of Formula (XIb):

Formula (XIb)

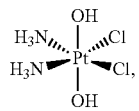

with the N-hydroxysuccinimide(NHS)-ester of Formula (XIIa) comprising:
a) suspending the platinum complex precursor in a reaction solvent which is preferably DMSO and adding the NHS-ester in particular in reaction solvent, in particular under stirring, wherein the molar ratio of the platinum complex precursor and NHS-ester is between about 0.6:1 and about 2:1, in particular the molar ratio is about 1:1;
b) stirring the mixture after step a) for at least about 8 h, in particular for at least about 24 h and further preferred for at least about 72 h at a temperature between about 20° C. and about 30° C., such as at about 25±2° C.;
(iii) isolating the platinum(IV) complex of Formula (IIa) comprising filtering the mixture after step b) for obtaining a filtrate, adding a precipitation solvent which is in particular dichloromethane to the filtrate and after about 24 h, in particular after about 48 h washing the residue with a washing solvent which is in particular dichloromethane.

In another particular embodiment, the method is for preparing a platinum(IV) complex of Formula (IIb) and the method comprises steps of:
(i) optionally preparing an N-hydroxysuccinimide(NHS)-ester of Formula (XIIa):

Formula (XIIa)

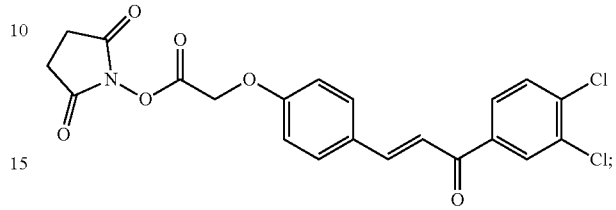

comprising:
a) providing a mixture of a compound of Formula (XIVa) and 1-ethyl-3-(3-dimethylaminopropyl)-carbodiimide (EDC) and N-hydroxysuccinimide (NHS):

Formula (XIVa)

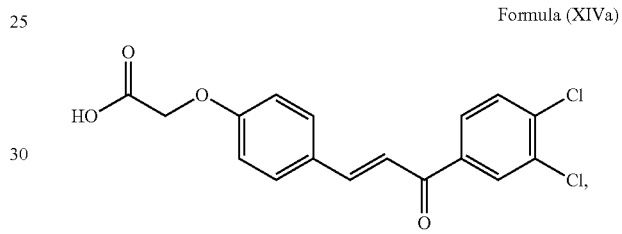

and stirring the mixture in a reaction solvent such as acetonitrile at a temperature between about 20° C. and about 30° C., such as at about 25±2° C., for at least about 8 h, in particular for at least about 10 h;
b) isolating the NHS-ester in particular comprising filtering the mixture for obtaining a residue and washing the residue with water and optionally freeze-drying the residue;
(ii) reacting a platinum complex precursor of Formula (XIc):

Formula (XIc)

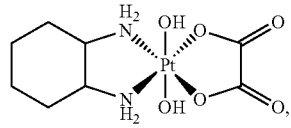

with an N-hydroxysuccinimide(NHS)-ester of Formula (XIIa) comprising:
a) suspending the platinum complex precursor and the NHS-ester in a reaction solvent which is preferably DMSO, wherein the molar ratio of the platinum complex precursor and the NHS-ester is between about 1:15 and about 1:5, in particular the molar ratio is about 1:10;
b) stirring the mixture after step a) for at least about 8 h, in particular for at least about 12 h such as for at least about 24 h at a temperature of at least 60° C. and in particular of between about 75° C. and about 85° C.;
(iii) isolating the platinum(IV) complex of Formula (IIb) comprising filtering the mixture after step b) for obtaining a filtrate, adding a precipitation solvent which is in particular a mixture of dichloromethane and diethyl ether to the filtrate and after about 24 h, in particular after about 48 h washing the residue with a washing solvent which is in particular dichloromethane.

In a further particular embodiment, the method is for preparing a platinum(IV) complex of Formula (IIIa) and the method comprises steps of:

(i) optionally preparing an N-hydroxysuccinimide(NHS)-ester of Formula (XIIIa):

Formula (XIIIa)

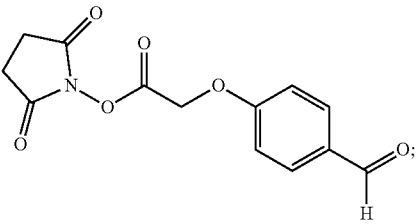

comprising:

a) providing a mixture of a compound of Formula (XVa) and 1-ethyl-3-(3-dimethylaminopropyl)-carbodiimide (EDC) and N-hydroxysuccinimide (NHS):

Formula (XVa)

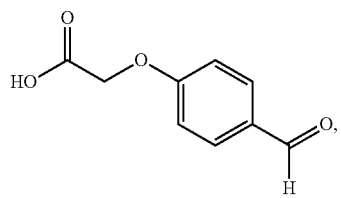

and stirring the mixture in a reaction solvent such as acetonitrile at a temperature between about 20° C. and about 30° C., such as at about 25±2° C., for at least about 8 h, in particular for at least about 10 h;

b) isolating the NHS-ester in particular comprising filtering the mixture for obtaining a residue and washing the residue with water and optionally freeze-drying the residue;

(ii) reacting a platinum complex precursor of Formula (XIb):

Formula (XIb)

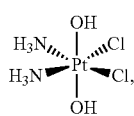

with an N-hydroxysuccinimide(NHS)-ester of Formula (XIIIa):
comprising
a) suspending the platinum complex precursor in a reaction solvent which is preferably DMSO and adding the NHS-ester in particular in reaction solvent, in particular under stirring, wherein the molar ratio of the platinum complex precursor and the NHS-ester is between about 0.6:1 and about 2:1, in particular the molar ratio is about 1:1;

b) stirring the mixture after step a) for at least about 8 h, in particular for at least about 24 h and further preferred for at least about 72 h at a temperature between about 20° C. and about 30° C., such as at about 25±2° C.;

(iii) isolating the platinum(IV) complex of Formula (IIIa) comprising filtering the mixture after step b) for obtaining a filtrate, adding a precipitation solvent which is in particular a mixture of dichloromethane and diethyl ether to the filtrate and after about 24 h, in particular after about 48 h washing the residue with a washing solvent which is in particular dichloromethane.

In a further particular embodiment, the method is for preparing a platinum(IV) complex of Formula (IIIb) and the method comprises steps of:

(i) optionally preparing an N-hydroxysuccinimide(NHS)-ester of Formula (XIIIa):

Formula (XIIIa)

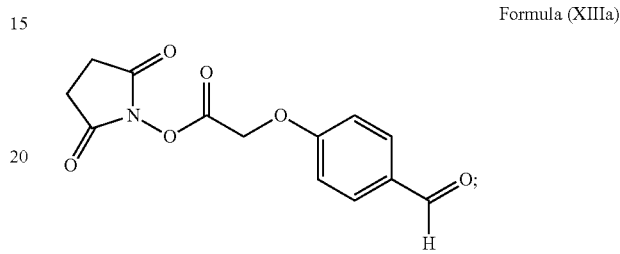

comprising:

a) providing a mixture of a compound of Formula (XVa) and 1-ethyl-3-(3-dimethylaminopropyl)-carbodiimide (EDC) and N-hydroxysuccinimide (NHS):

Formula (XVa)

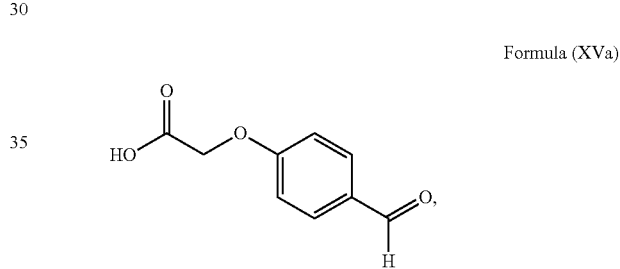

and stirring the mixture in a reaction solvent such as acetonitrile at a temperature between about 20° C. and about 30° C., such as at about 25±2° C., for at least about 8 h, in particular for at least about 10 h;

b) isolating the NHS-ester in particular comprising filtering the mixture for obtaining a residue and washing the residue with water and optionally freeze-drying the residue;

(ii) reacting a platinum complex precursor of Formula (XIb):

Formula (XIb)

with an N-hydroxysuccinimide(NHS)-ester of Formula (XIIIa) comprising:

a) suspending the platinum complex precursor and the NHS-ester in a reaction solvent which is preferably DMSO, wherein the molar ratio of the platinum complex precursor and NHS-ester is between about 1:15 and about 1:5, in particular the molar ratio is about 1:10;

b) stirring the mixture after step a) for at least about 8 h, in particular for at least about 12 h such as for at least about 24 h at a temperature of at least 60° C. and in particular of between about 75° C. and about 85° C.;

(iii) isolating the platinum(IV) complex of Formula (IIIb) comprising filtering the mixture after step b) for obtaining a filtrate, adding a precipitation solvent which is in particular a mixture of dichloromethane and diethyl ether to the filtrate and after about 24 h, in particular after about 48 h washing the residue with a washing solvent which is in particular dichloromethane.

In a further particular embodiment, the method is for preparing a platinum(IV) complex of Formula (IIIc) and the method comprises steps of:

(i) optionally preparing an N-hydroxysuccinimide(NHS)-ester of Formula (XIIIa):

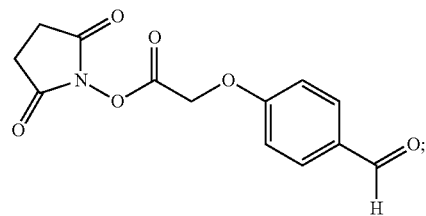

Formula (XIIIa)

comprising:

a) providing a mixture of a compound of Formula (XVa) and 1-ethyl-3-(3-dimethylaminopropyl)-carbodiimide (EDC) and N-hydroxysuccinimide (NHS):

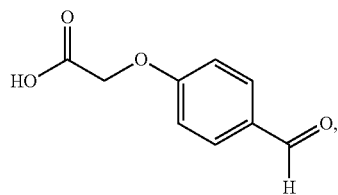

Formula (XVa)

and stirring the mixture in a reaction solvent such as acetonitrile at a temperature between about 20° C. and about 30° C., such as at about 25±2° C., for at least about 8 h, in particular for at least about 10 h;

b) isolating the NHS-ester in particular comprising filtering the mixture for obtaining a residue and washing the residue with water and optionally freeze-drying the residue;

(ii) reacting a platinum complex precursor of Formula (XIc):

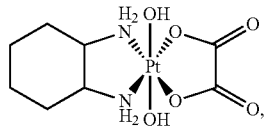

Formula (XIc)

with an N-hydroxysuccinimide(NHS)-ester of Formula (XIIIa) comprising:

a) suspending the platinum complex precursor in a reaction solvent which is preferably DMSO and adding the NHS-ester in particular in the reaction solvent, in particular under stirring, wherein the molar ratio of the platinum complex precursor and NHS-ester is between about 0.6:1 and about 2:1, in particular the molar ratio is about 1:1;

b) stirring the mixture after step a) for at least about 8 h, in particular for at least about 24 h and further preferred for at least about 72 h at a temperature between about 20° C. and about 30° C., such as at about 25±2° C.;

(iii) isolating the platinum(IV) complex of Formula (IIIc) comprising filtering the mixture after step b) for obtaining a filtrate, adding a precipitation solvent which is in particular a mixture of dichloromethane and diethyl ether to the filtrate and after about 24 h, in particular after about 48 h washing the residue with a washing solvent which is in particular dichloromethane.

The present invention in a third aspect refers to a method for treating a subject suffering from a disease comprising administering an effective amount of a platinum complex as described above to said subject, i.e. comprising administering a platinum(IV) complex comprising a structure of Formula (I) to said subject:

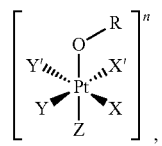

Formula (I)

with X, X', Y, Y' and Z, n and R as defined above and with the provision that the platinum complex is not chalcoplatin, i.e. with the proviso that the platinum complex does not have the following structure:

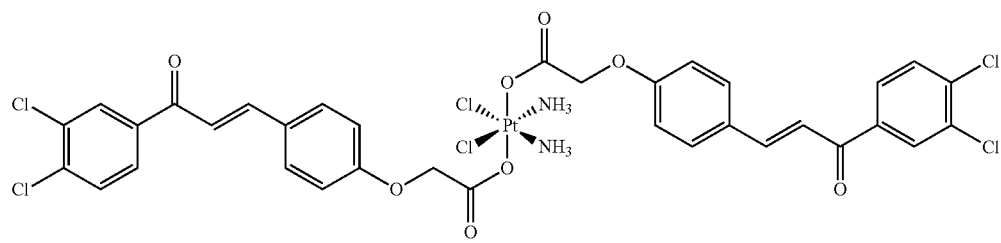

This means a proviso that when R is

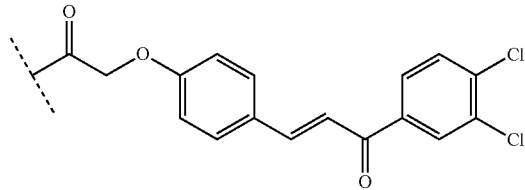

and either the ligands Y and Y' are amine (NH$_3$) each and X and X' are chlorido each or if Y and Y' are chlorido each and X and X' are amine (NH$_3$) each, Z is not —OR.

The disease is in particular a tumor and in particular a cancer, for example, but not limited to one of:

an ovarian cancer, a lung cancer, a breast cancer, or a colorectal cancer.

le;2qThe term "tumor" simply refers to all neoplastic cell growth and proliferation being of benign (generally harmless) or malignant (cancerous) growth, and all pre-cancerous and cancerous cells and tissues. The terms "cancer" and "cancerous" describe a physiological condition in subjects in which a population of cells are characterized by unregulated malignant (cancerous) cell growth.

The cancer can be a cancer which has a natural, i.e. intrinsic, or acquired resistance against one or more chemotherapeutic compounds in particular which has a natural or has an acquired, i.e. developed resistance against known coordination complexes of platinum such as cisplatin. A cancer is resistant against one or more chemotherapeutic compounds if it comprises cancer cells which are resistant against said chemotherapeutic compounds. Accordingly, the cancer cells with a resistant phenotype will be less sensitive or more tolerant to the one or more chemotherapeutic compounds. Such cancer or cancer cells can be detected in a subject, cancer or tissue by administering to the subject, tissue, or cell, the one or more chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have the resistance against the chemotherapeutic compound or non-cancerous cells. This can be determined, for example, by means of an MTT assay. A cancer or cancer cells which have a natural (intrinsic) or acquired resistance against cisplatin are referenced herein as "cisplatin-resistant".

In particular embodiments of the present invention, the cancer has a natural or an acquired resistance against cisplatin, also known as cDDP (cis-diaminedichloroplatinum).

The term "subject" used herein refers to a living organism and can include but is not limited to a human, a plant and an animal. The subject is preferably a human or an animal, in particular the subject is a mammal, preferably a human. The subject is preferably a human having a cancer.

The platinum(IV) complex administered, thus, comprises a structure selected from one of Formulas (II) to (X):

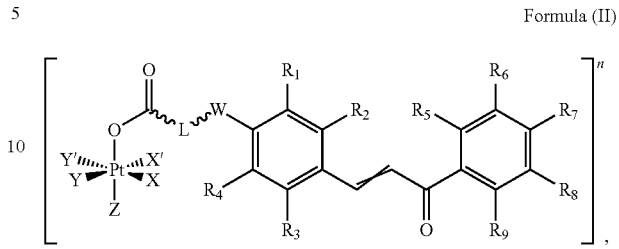

Formula (II)

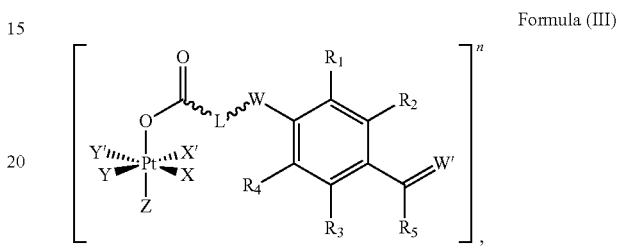

Formula (III)

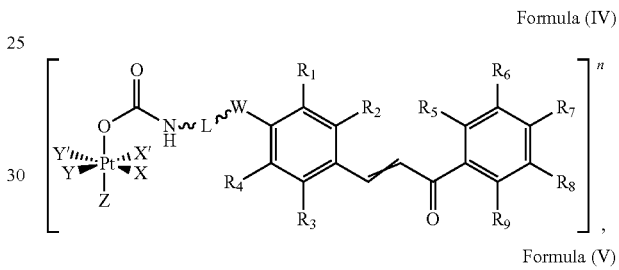

Formula (IV)

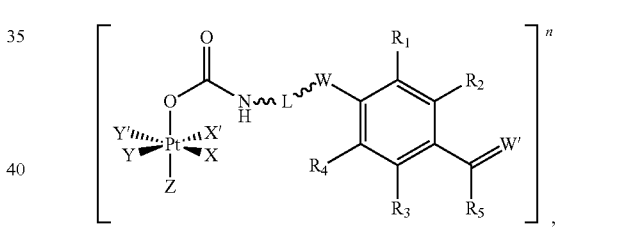

Formula (V)

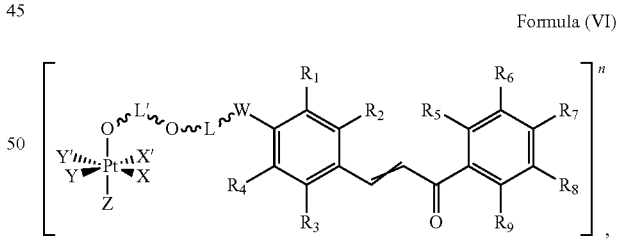

Formula (VI)

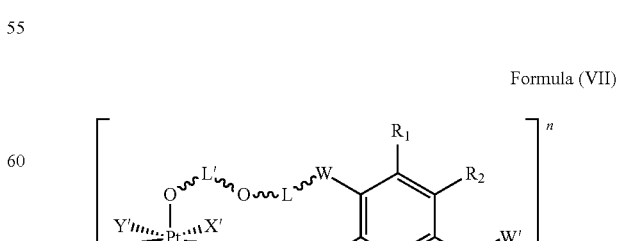

Formula (VII)

Formula (VIII)
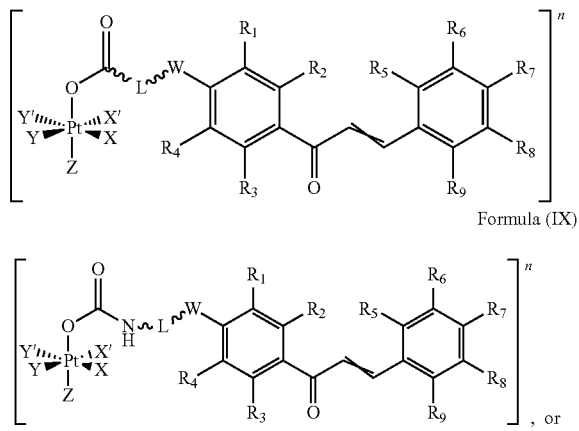
Formula (IX)
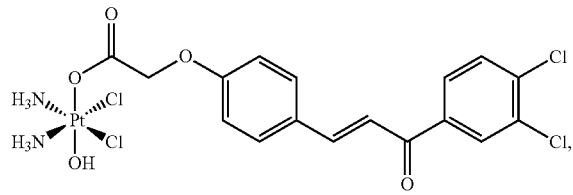
, or
Formula (X)
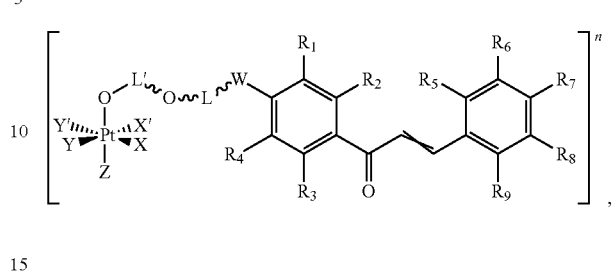
,
wherein X, X', Y, Y', Z, L, L', W, W', n and $R_1$ to $R_9$ are as defined above.
In particular, the platinum(IV) complex administered can comprise a structure selected from:
Formula (IIa)
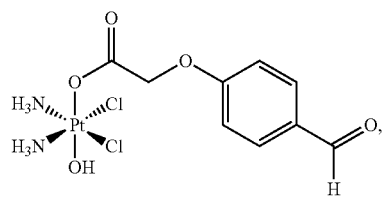
Formula (IIb)
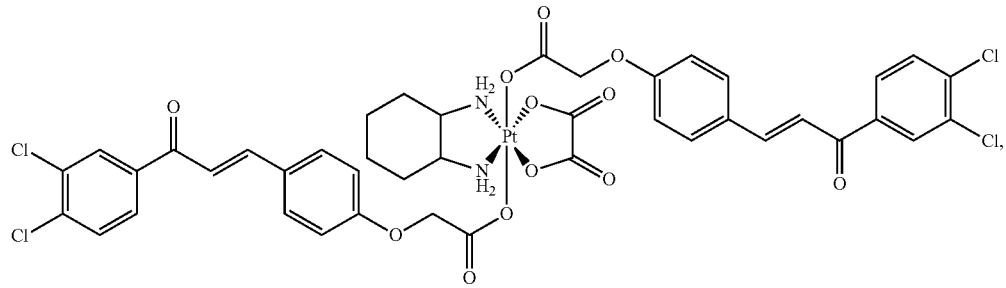
Formula (IIIa)
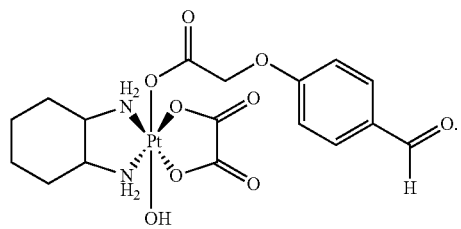
Formula (IIIb)
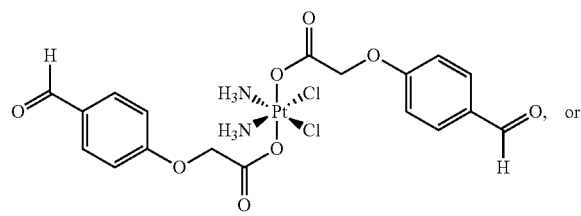
, or
Formula (IIIc)

Most preferably, the platinum(IV) complex comprises a structure of Formula (II), in particular of Formula (IIa):

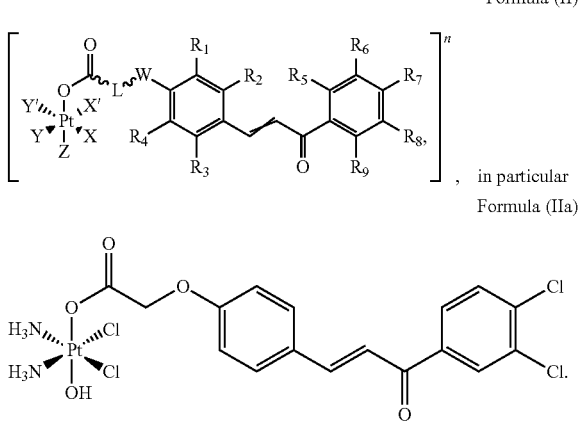

Formula (II)

, in particular Formula (IIa)

The platinum(IV) complex can be, for example, present in form of a pharmaceutically acceptable salt or a solvate.

The expression "effective amount" and "effective dose" generally denote an amount sufficient to produce therapeutically desirable results, wherein the exact nature of the result varies depending on the specific disorder which is treated. When the disorder is a tumor such as cancer, the result is usually an inhibition or suppression of the proliferation of the cancer or tumor cells, a reduction of cancerous cells or the amelioration of symptoms related to the cancer cells.

The effective amount of the platinum(IV) complex of the present invention may depend on the species, body weight, age and individual conditions of the subject and can be determined by standard procedures such as with cell cultures or experimental animals. A concentration of the platinum (IV) complex may, for example, be at least about 10 nm.

Preferably, the $IC_{50}$ of the platinum(IV) complex towards tumor cells such as cancer cells is at most 1000 nM, in particular it is less than 500 nM and further preferred less than 200 nM and most preferably less than 200 nM after about 72 h in particular towards cancer cells from one of an ovarian cancer, a lung cancer, a breast cancer, or a colorectal cancer including cisplatin resistant cancer. The Resistant Factor of the platinum(IV) complex of the present invention towards cisplatin-resistant cancer cells is preferably less than 10, more preferably less than 8 and in particular even less than 5. The Resistant Factor is calculated by dividing the $IC_{50}$ of the platinum complex towards cisplatin-resistant cells by its $IC_{50}$ towards cancer cells of the same cell type or tissue which do not have a cisplatin-resistant phenotype.

The platinum(IV) complex can be present in solid, semisolid or liquid form. The platinum(IV) complex of the present invention can be administered by an oral or parenteral route to the subject, in particular by an oral route or an intravenous route.

The platinum(IV) complex may be administered in form of a pharmaceutical composition comprising the platinum complex and a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof. A person of skill in the art is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition can be present in solid, semisolid or liquid form to be administered by an oral or parenteral route to the subject.

In an embodiment, the platinum(IV) complex can be used as a single compound for treating the subjects in particular with cancer.

In other embodiments, the platinum(IV) complex is administered in combination with other therapeutically effective treatments such as one or more of:

other therapeutically effective compounds such as chemotherapeutic compounds including, for example, a topoisomerase-II inhibitor, an anthracycline, a coordination complex of platinum, a taxane, a protein kinase inhibitor, a *vinca* alkaloid or derivative thereof, a topoisomerase-I inhibitor and a nucleotide analog or precursor analog;

radiation therapy;

hormonal therapy; and/or targeted therapy including immunotherapy such as monoclonal antibody therapy.

The present invention further provides a pharmaceutical composition comprising:

(i) a platinum(IV) complex of the present invention; and (ii) a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof.

The pharmaceutical composition can be present in solid, semisolid or liquid form to be administered by an oral or parenteral route to a subject. "Pharmaceutically tolerable excipients" are those which can be taken by the subject without therapeutically relevant adverse effects and do not negatively influence the efficiency of the platinum complex.

According to the invention is also the platinum(IV) complex described above, in particular of Formula (IIa), for use as a medicament for the treatment of cancer. The platinum (IV) complex such as of Formula (IIa) can be used in an effective amount for treating an animal or a human, in particular mammal, preferably a human. Another aspect of the invention refers to the use of the platinum(IV) complex described above in particular of Formula (IIa) for preparing a medicament for treatment of cancer. The platinum(IV) complex described above in particular of Formula (IIa) may be used in combination with at least a further chemotherapeutic compound.

In another aspect, the invention provides a method for inhibiting the growth of tumor cells. Said method comprises the step of contacting a population of tumor cells such as a population of cancer cells with the platinum(IV) complex described above which can, for example, be a salt or solvate. Preferably, the cell growth is reduced and/or cell death is induced. MTT assay can be used for confirming the effect on cell death and cell viability.

For example, inhibiting the growth of tumor cells can mean a decrease in the cell viability in particular a significant decrease and/or an increase in the number of apoptotic cells, in particular a significant increase. The skilled person is aware of methods for verifying such effects such as with cell viability measurement by means of a MTS proliferation assay, a MTT assay or by determination of the apoptosis rate by means of Annexin V flow cytometry measurement. As used herein, the term "significant" means that is statistically significant as determined by Student's t-test or other art-accepted measures of statistical significance.

In particular, the platinum(IV) complex administered can comprise a structure selected from:

Formula (IIa)

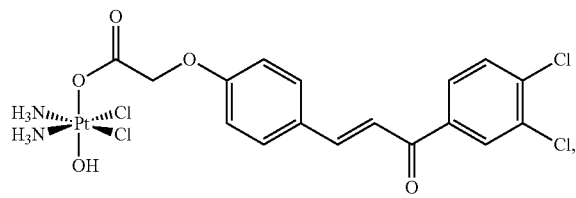

Formula (IIb)

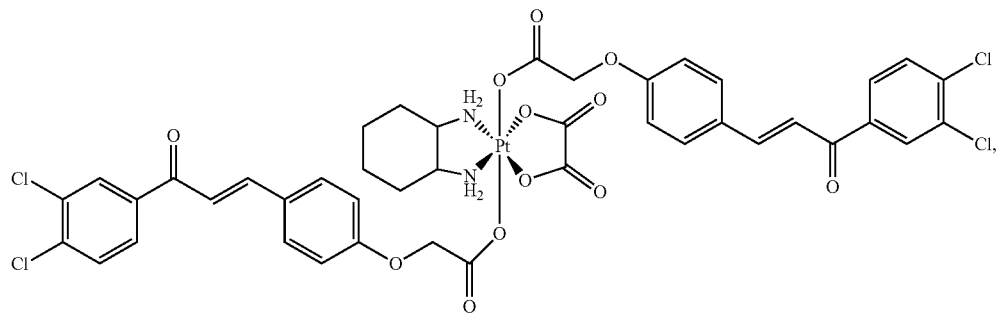

Formula (IIIa)

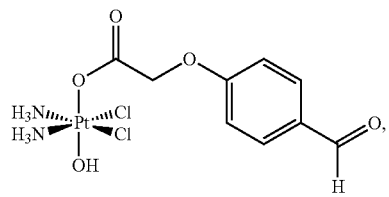

Formula (IIIb)

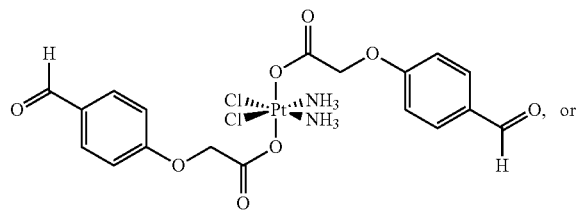, or

Formula (IIIc)

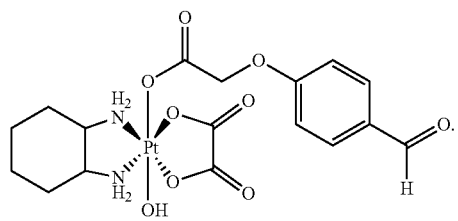

Most preferably, the platinum(IV) complex comprises a structure of Formula (II), in particular of Formula (IIa):

Formula (II)

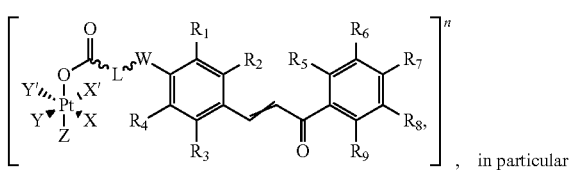, in particular

Formula (IIa)

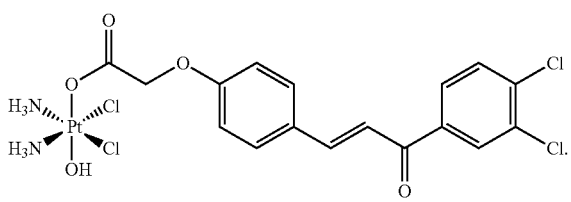

The cells can, for example, but not limited to be from one of:
an ovarian cancer,
a lung cancer,
a breast cancer, or
a colorectal cancer.

The cancer cells can have a natural or an acquired resistance against one or more chemotherapeutic compounds, in particular a natural or an acquired resistance against known coordination complexes of platinum such as cisplatin. Preferably, the $IC_{50}$ of the platinum complex towards the cancer cells is less than 500 nM and further preferred less than 200 nM and most preferably less than 200 nM after about 72 h in particular towards one of an ovarian cancer, a lung cancer, a breast cancer, or a colorectal cancer including cisplatin-resistant cancers. The Resistant Factor of the platinum(IV) complex of the present invention towards cisplatin-resistant cancer cells is preferably less than 8 and in particular even less than 5.

The step of contacting the tumor cells with the platinum (IV) complex of the present invention may be carried out by applying an incubation solution comprising the platinum (IV) complex to said cells which incubation solution may further comprise suitable excipients such as buffers or a suitable growth medium. Alternatively, contacting the tumor cells with the platinum(IV) complex of the present invention can be carried out by administering the platinum(IV) complex to a subject such as a mammal like a human, for example, by an oral or parenteral route in form of a pharmaceutical composition as described above.

EXAMPLES

Several highly cytotoxic platinum(IV) complexes of the present invention have been prepared and spectroscopically characterized. The anticancer effect of the complexes has been tested with different types of human cancer cells.

Example 1A

Preparation of platinum(IV) complexes of the present invention Platinum(IV) complexes of the present invention were prepared by reacting c,c,t-[Pt(NH$_3$)$_2$Cl$_2$(OH)$_2$] or [Pt(DACH)(OH)$_2$(ox)] (DACH=trans-(1R,2R)-1,2-cyclohexanediamine, ox=oxalato) with the NHS-ester of the corresponding aryl-comprising moiety at different reaction conditions. All reactions described herein were carried out under protection of Argon unless otherwise noted. Agents and solvents were used as received without further drying or purification without further notification.

Platinum contents were tested by an inductively coupled plasma-optical emission spectrometer (ICP-OES, Optima 2100DV, PerkinElmer, USA). Elemental analysis was performed on a vario micro elemental analyzer. $^1$H, $^{13}$C, and $^{195}$Pt NMR spectra were measured by a Bruker Ultrashield™ 300, 400, or 600 MHz NMR spectrometer at ambient temperature. All NMR chemical shifts (δ) are reported in parts per million (ppm) and referenced as described below. $^1$H and $^{13}$C NMR spectra were referenced internally to residual solvent peaks using deuterated dimethyl sulfoxide (DMSO-d6), or deuterated chloroform (CDCl$_3$) as the solvents. $^{195}$Pt NMR spectrum was referenced by using external standards of K$_2$PtCl$_4$ in D$_2$O (δ=−1628 ppm).

Synthesis of the Platinum(IV) Complex Having Formula (IIa) (Further Referenced as "MonochalcoPt(IV) or "Monochalcoplatin")

Synthesis of the respective NHS ester (referred to as "chalcone NHS-ester"): Chalcone (675.0 mg, 1.92 mmol), 1-ethyl-3-(3-dimethylaminopropyl)-carbodiimide (EDC) (265.7 mg, 2.31 mmol), and N-hydroxysuccinimide (NHS) (442.3 mg, 2.31 mmol) were stirred in 70 mL acetonitrile at r.t. overnight. The white suspension was collected by filtration. EDC/NHS was removed by washing with H$_2$O. White powder was obtained after freeze drying. Pale powder. 550.0 mg, yield 64.0%.

Synthesis of monochalcoPt(IV) from the chalcone NHS-ester: c,c,t-[Pt(NH$_3$)$_2$Cl$_2$(OH)$_2$](245.8 mg, 0.74 mmol) was suspended in 10 mL DMSO. 20 mL DMSO solution of the chalcone NHS-ester (330.0 mg, 0.74 mmol) was added slowly to the stirred suspension. The reaction mixture was stirred vigorously at r.t. for 72 h. The unreacted c,c,t-[Pt(NH$_3$)$_2$Cl$_2$(OH)$_2$] was removed by filtration, then a large amount of dichloromethane (DCM) was added to the bright yellow solution to get light yellow precipitate. After 48 h, the precipitate was collected by filtration and washed with DCM (5 mL×3). Yellow powder. 256.0 mg, 51.0%. $^1$H NMR (400 MHz, DMSO-d6) δ ppm 8.41 (s, 1H), 8.12 (d, J=8.4 Hz, 1H), 7.93-7.71 (m, 5H), 7.01 (d, J=8.4 Hz, 2H), 6.22-5.74 (m, 6H, NH3), 4.62 (s, 2H), 1.18 (s, 1H, OH). $^{13}$C NMR (100 MHz, DMSO-d6) δ ppm 186.8, 175.2, 160.7, 145.3, 138.0, 135.8, 131.9, 131.1, 131.0, 130.3, 128.5, 127.2, 118.7, 115.2, 65.8. $^{195}$Pt NMR (129 MHz, DMSO-d6): δ ppm 1050. MS (ESI+) m/z: MS (ESI−) m/z: [M-H]− calculated for C$_{17}$H$_{17}$N$_2$O$_5$Cl$_4$Pt: 664.95, found: 664.95. Anal. Calcd for C$_{19}$H$_{26}$Cl$_4$N$_2$O$_7$PtS: C, 29.90; H, 3.43; N, 3.67. Found: C, 30.24, H, 3.98, N, 4.04.

FIG. 1 summarizes the synthesis route of monochalcoPt(IV) wherein (2) is 4-formylphenoxyacetic acid ("4-formylphenoxyacetic"); i: 50% KOH solution, r.t., 12 h; ii: diluted HCl solution, r.t., 6 h. Pale powder, 80.0%.

Synthesis of the Platinum(IV) Complex Having Formula (IIb) (Further Referenced as Dichalco-oxaliPt(IV))

1.0 equivalent [Pt(DACH)(OH)$_2$(ox)] (50 mg, 0.12 mmol) and 10.0 equivalent chalcone NHS-ester of (519.6 mg, 1.2 mmol) were suspended in 10 mL DMSO. The reaction mixture was stirred vigorously at 75-85° C. for 24 h. The unreacted [Pt(DACH)(OH)$_2$(ox)] was removed by filtration, then a large amount of dichloromethane (DCM) and diethyl ether was added to the bright yellow solution to get light yellow precipitate. After 48 h, the precipitate was collected by filtration and washed with DCM (5 mL×3). Light yellow powder was obtained in a reasonable yield. 20.2 mg, 15.7%. $^1$H NMR (400 MHz, DMSO-d6) δ 8.40 (s, 1H), 8.40-8.34 (m, 1H), 8.11 (d, J=8.4 Hz, 1H), 8.02-7.65 (m, 6H), 6.97 (d, J=8.0 Hz, 2H), 4.79 (s, 2H), 2.08-2.05 (m, 1H), 1.48-1.40 (m, 2H), 1.11-1.05 (m, 1H).

Figure 2:
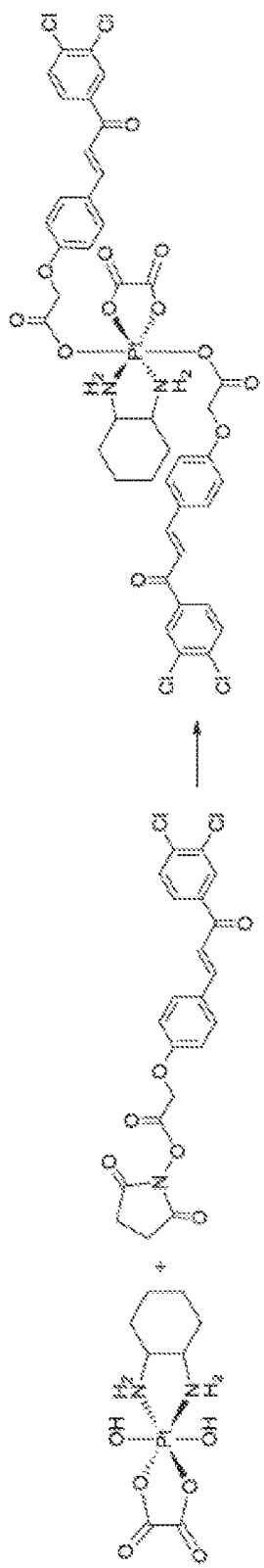
FIG. 2 summarizes the synthesis route of dichalco-oxaliPt (IV)

FIG. 2 summarizes the synthesis route of dichalco-oxaliPt(IV).

Synthesis of the Platinum(IV) Complex Having Formula (IIIa) (Further Referenced as "Mono4FP-Pt(IV)")

Synthesis of 4-formylphenoxyacetic (4FP acid) NHS-ester: 4-formylphenoxyacetic (500 mg, 2.76 mmol), 1-ethyl-3-(3-dimethylaminopropyl)-carbodiimide (EDC) (638.4 mg, 3.33 mmol), and N-hydroxysuccinimide (NHS) (383.3 mg, 3.33 mmol) were stirred in 70 mL acetonitrile at r.t. overnight. The white suspension was collected by filtration. EDC/NHS was removed by washing with H$_2$O. White powder. 630.0 mg, 82.0%. $^1$H NMR (400 MHz, DMSO-d6) δ 9.91 (s, 1H), 7.95-7.85 (d, J=8.0, 2H), 7.26-7.18 (d, J=8.0, 2H), 5.51 (s, 2H), 2.84 (s, 4H).

Synthesis of mono4FP-Pt(IV) from the 4FP acid NHS-ester: c,c,t-[Pt(NH$_3$)$_2$Cl$_2$(OH)$_2$](100.0 mg, 0.3 mmol) was suspended in 5 mL DMSO. NHS ester of 4FP acid (83.0 mg, 0.3 mmol) was dissolved in 10 mL DMSO and was added dropwise. The reaction mixture was stirred vigorously at r.t. for 72 h or more. The unreacted c,c,t-[Pt(NH$_3$)$_2$Cl$_2$(OH)$_2$] was removed by filtration, then a large amount of dichloromethane (DCM) and diethyl ether was added to the bright yellow solution to get light yellow precipitate. After 48 h, the precipitate was collected by filtration and washed with DCM (5 mL×3). Yellow powder. 70.0 mg, yield 47.0%. $^1$H NMR (400 MHz, DMSO-d6) δ 9.87 (s, 1H), 7.82 (d, J=8.0 Hz, 2H), 7.11 (d, J=8.0 Hz, 2H), 6.23-5.74 (m, 6H), 4.66 (s, 2H), 1.18 (s, 1H).

Figure 3:
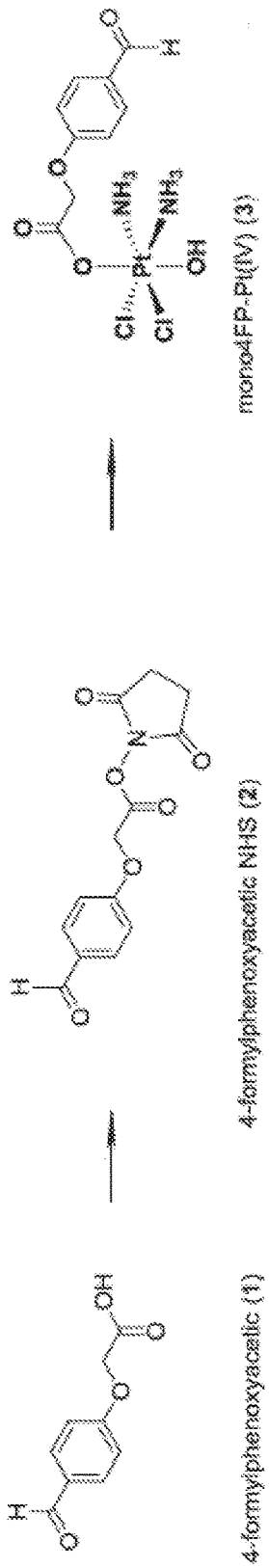
FIG. 3 summarizes the synthesis route of mono4FP-Pt (IV)

FIG. 3 summarizes the synthesis route of mono4FP-Pt(IV).

Synthesis of the Platinum(IV) Complex Having Formula (IIIb) (Further Referenced as "di4FP-Pt(IV)")

c,c,t-[Pt(NH$_3$)$_2$Cl$_2$(OH)$_2$] (100.0 mg, 0.3 mmol) and the NHS ester of 4FP acid (833.3 mg, 3.0 mmol) were suspended in 10 mL DMSO. The reaction mixture was stirred vigorously at 75-85° C. for 24 h or more. The unreacted c,c,t-[Pt(NH$_3$)$_2$Cl$_2$(OH)$_2$] was removed by filtration, then a large amount of dichloromethane (DCM) and diethyl ether was added to the bright yellow solution to get light yellow precipitate. After 48 h, the precipitate was collected by filtration and washed with DCM (5 mL×3). 140.0 mg, yield 70.8%. $^1$H NMR (400 MHz, DMSO-d6) δ 9.88 (s, 1H), 7.83 (d, J=8.4 Hz, 2H), 7.13 (d, J=8.0 Hz, 2H), 6.85-6.32 (m, 3H), 4.80 (s, 2H). Yellow powder.

Figure 4:
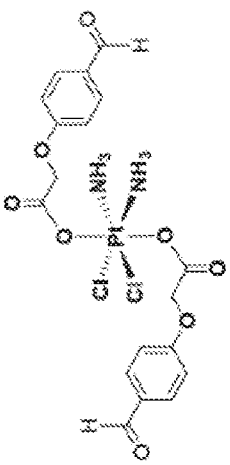
FIG. 4 summarizes the synthesis route of di4FP-Pt(IV)
Figure 4:
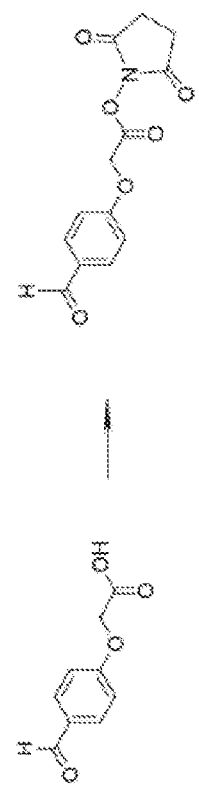

FIG. 4 summarizes the synthesis route of di4FP-Pt(IV).

Synthesis of the Platinum(IV) Complex Having Formula (IIIc) (Further Referenced as "mono4FP-oxaliPt(IV)")

[Pt(DACH)(OH)$_2$(ox)] (50.0 mg, 0.12 mmol) was suspended in 5 mL DMSO. NHS ester of 4FP acid (32.2 mg, 0.12 mmol) was dissolved in 10 mL DMSO and was added dropwise. The reaction mixture was stirred vigorously at r.t. for 72 h or more. The unreacted [Pt(DACH)(OH)$_2$(ox)] was removed by filtration, then a large amount of dichloromethane (DCM) and diethyl ether was added to the bright yellow solution to get light yellow precipitate. After 48 h, the precipitate was collected by filtration and washed with DCM (5 mL×3). Yellow powder, 15.0 mg, 21.8%. $^1$H NMR (400 MHz, DMSO-d6) δ 9.86 (s, 1H), 8.20-7.87 (m, 3H), 7.82 (d, J=8.0 Hz, 2H), 7.16-7.11 (m, 1H), 7.04 (d, J=8.30 Hz, 2H), 4.72 (s, 2H), 2.65 (s, 1H), 2.46-2.44 (m, 2H), 2.04 (t, J=14.5 Hz, 2H), 1.55-0.90 (m, 6H). $^{13}$C NMR (100 MHz, DMSO-d6) δ 191.8, 176.0, 164.2, 163.4, 132.1, 130.2, 115.5, 66.6, 61.8, 60.6, 40.9, 31.3, 31.1, 24.1, 24.0.

Figure 5:
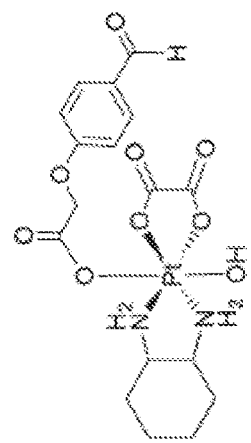
FIG. 5 summarizes the synthesis route of mono4FP-oxaliPt(IV).
Figure 5:
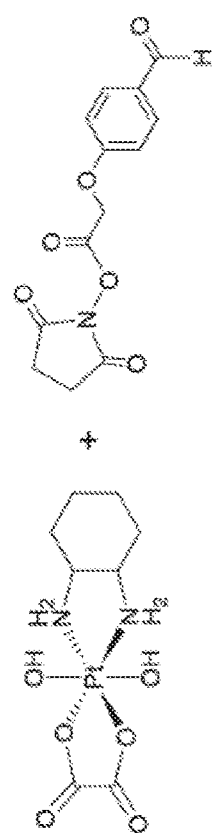

FIG. 5 summarizes the synthesis route of mono4FP-oxaliPt(IV).

Example 1B

Cytotoxicity Analysis of the Platinum(IV) Complexes of the Present Invention

Cell Lines and Cell Culture Conditions

Human ovarian carcinoma A2780 and cisplatin-resistant A2780cisR cells were cultured in RPMI 1640 with 10% FBS and 100 units penicillin/streptomycin. Human breast adenocarcinoma MCF-7, human colorectal carcinoma HCT116, human lung carcinoma A549, and cisplatin-resistant A549cisR cells were cultured in DMEM containing 10% FBS and 100 units penicillin/streptomycin. Human fetal lung fibroblast MRC-5 cells were cultured in MEM with 10% FBS, 1% L-glutamine, 1% non-essential amino acids, and 1% sodium pyruvate. Cisplatin-resistant cells, A549cisR and A2780cisR, were generated from their parental A549 or A2780 cells. Briefly, A549 or A2780 cells were cultured in complete medium containing 0.5 μg/mL cisplatin at the beginning for the first screening, and the remaining cells were cultured in complete medium containing 1.0 μg/mL cisplatin for at least 4 weeks until the resistance was obtained. All cells were incubated at 37° C. in 5% CO$_2$.

Cytotoxicity Test

An MTT assay was used to evaluate the cytotoxicity of cisplatin (cDDP), the platinum(IV) complex of the present invention of Formula (IIa) (monochalcoPt(IV)), chalcoplatin and cDDP combined with one equivalent ligand chalcone against A2780, A2780cisR, A549, A549cisR, MFC-7 and MRC-5 cells.

For each of these assays, cells were seeded in 96-well plates at a certain density. For instance, A2780 cells were seeded in a 96-well plate at the density of 1,500 cells per well and incubated till the confluence reached about 30%. Cells were then treated with medium containing varying concentrations of compounds for 72 h at 37° C. in 5% CO$_2$. DMF was used to increase the solubility of compounds, and the final concentration of DMF was 1% (V/V). For MTT assay, after incubation for 72 h, the medium containing compounds was replaced by FBS-free medium with 1 mg/mL MTT for 4 h incubation. DMSO was added to each well when the medium containing MTT was removed after incubation. The absorbance was measured at 570 and 630 nm. Cells incubated with medium containing 1% DMF only were used as controls. The seeded cell density for A549, MCF-7 and HCT116 was 1,500 cells/well, and for A2780cisR, A549cisR, and MRC-5 was 2,500 cells were seeded to each well. The absorbance was tested at 570 and 630 nm.

The results of this assay are presented in Table 1 depicting the resulting cytotoxicity of monochalcoPt(IV) compared to the cytotoxicity of cDDP, chalcoplatin and cDDP combined with a chalcone ligand. The IC$_{50}$ values represent the concentration of the tested compound required to inhibit cell growth by 50% compared to controls run in the absence of added complexes, measured by the MTT assay following a 72 h exposure. Values are the average of the 96-wells for each tested compound, and the reported errors are the corresponding standard deviations. In Table 1 the FI (fold increase) is defined as IC$_{50}$(cDDP)/IC$_{50}$(monochalcoPt(IV)), and the RF (resistant factor) is defined as the respective IC$_{50}$ of a tested compound in A2780cisR/IC50 in A2780 cells, or IC$_{50}$ in A549cisR/IC$_{50}$ in A549 cells.

As seen in Table 1, monochalcoPt(IV) is significantly more active than both cisplatin (cDDP) and chalcoplatin, and the IC$_{50}$ values of monochalcoplatin are in the nanomolar range in all the cells tested. For example, the IC$_{50}$ values of chalcoplatin in A2780 and A549 cells are 830 and 1900 nM, respectively, while those of monochalcoPt(IV) are as low as 10 nM and 80 nM, respectively. Compared with cisplatin, monochalcoPt(IV) displays up to a 422-fold increase in cytotoxicity in the cells tested. Furthermore, monochalcoPt(IV) is able to overcome cisplatin resistance. MonochalcoPt(IV) displays nanomolar cytotoxicity in both A2780cisR and A549cisR cells. In A549 and A549cisR cells, the RF value is 4.3 for cisplatin, and the value decreases to 1.8 for monochalcoPt(IV). A similar trend is also found in A2780 and A2780cisR cells. MonochalcoPt (IV) is also very active against the proliferation of MCF-7 and HCT116 cells, and the FI value for HCT116 cells is as high as 421.9. MRC-5, the human lung fibroblast cell line, was used to evaluate the cytotoxicity of monochalcoPt(IV) against normal cells.

TABLE 1

Cytotoxicity of monochalcoPt(IV) compared to cisplatin (cDDP), cDDP with a chalcone ligand and chalcoplatin upon 72 h drug treatment in cancer cells by MTT assay (IC$_{50}$ in nM)

| Cell line | cDDP | Chalcone | cDDP + chalcone | chalcoplatin | monochalcoPt(IV) | FI[b] |
|---|---|---|---|---|---|---|
| A2780 | 830 ± 270 | >35000 | 490 ± 320 | 830 ± 570 | 10 ± 3 | 83 |
| A2780cisR | 13050 ± 2300 | >35000 | >2000 | 1590 ± 250 | 70 ± 10 | 186 |
| RF[a] | 16 | — | — | 1.9 | 7.0 | — |

TABLE 1-continued

Cytotoxicity of monochalcoPt(IV) compared to cisplatin (cDDP), cDDP with a chalcone ligand and chalcoplatin upon 72 h drug treatment in cancer cells by MTT assay (IC$_{50}$ in nM)

| Cell line | cDDP | Chalcone | cDDP + chalcone | chalcoplatin | monochalcoPt(IV) | FI[b] |
|---|---|---|---|---|---|---|
| A549 | 1380 ± 160 | >40000 | 580 ± 100 | 1900 ± 700 | 80 ± 10 | 17.3 |
| A549cisR | 5880 ± 420 | >40000 | 6860 ± 650 | 1600 ± 500 | 140 ± 10 | 42 |
| RF | 4.3 | — | 12 | 0.84 | 1.8 | — |
| MCF-7 | 18020 ± 400 | >50000 | 14060 ± 500 | 4800 ± 1000 | 240 ± 8 | 75.1 |
| HCT116 | 9703 ± 793 | N.D. | 8580 ± 653 | 1766 ± 141 | 23 ± 6 | 421.9 |
| MRC-5 | 4900 ± 200 | 65100 ± 9000 | 3090 ± 460 | 9000 ± 400 | 110 ± 30 | 44.5 |

[a]RF (Resistant Factor) is defined as IC$_{50}$ in A2780CisR/IC$_{50}$ in A2780 cells or as IC$_{50}$ in A549cisR/IC$_{50}$ in A549 cells
[b]FI (fold increase) is defined as IC$_{50}$(cDDP)/IC$_{50}$(monochalcoPt(IV))

The invention claimed is:

1. A platinum(IV) complex comprising a structure of Formula (I):

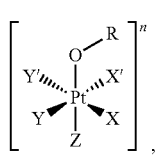

Formula (I)

wherein:

X, X', Y, Y' and Z are independently selected from an electron donor ligand and may be linked to each other in any combination;

n is selected from zero, any positive charge or any negative charge;

R is an aryl-comprising moiety selected from the group consisting of:

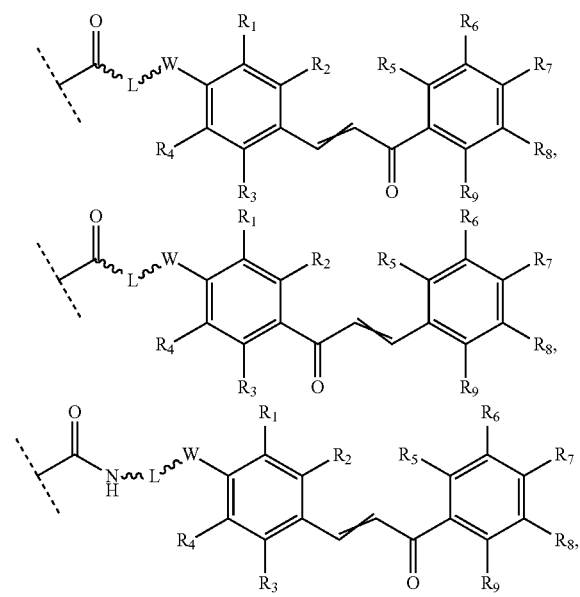

with L and L' being a linker group, W being a linker atom, and R$_1$ to R$_9$ being independently selected from a substituent or a hydrogen atom; and ≈ being a double bond covering the (E) and (Z) configuration; and with the provision that the platinum complex is not chalcoplatin.

2. The platinum(IV) complex of claim 1, wherein:

X, X', Y, Y' and Z are independently selected from a nitrogen-containing ligand, an oxygen-containing ligand, a phosphorous-containing ligand, a sulfur-containing ligand and a halogen containing ligand;

L is —(CH$_2$)$_m$— with m being an integer which is >0;

W is a heteroatom.

3. The platinum(IV) complex of claim 1, wherein:

X, X', Y and Y' are independently selected from ammine, aqua, a halido, hydroxido, oxalato or diamines and Z is selected from ammine, aqua, a halido, hydroxido, oxalato or diamines or —OR with R being as defined above;

L is —(CH$_2$)$_m$— with m being an integer selected from 1, 2, 3 or 4;

L' is —(CH$_2$)$_{m'}$— with mm' being an integer selected from 1, 2 or 3;

W is selected from an oxygen or a sulfur atom; and

R$_1$ to R$_9$ are independently selected from a hydrogen atom or a halogen atom.

4. The platinum(IV) complex of claim 1 which comprises the structure of Formula (II):

Formula (II)

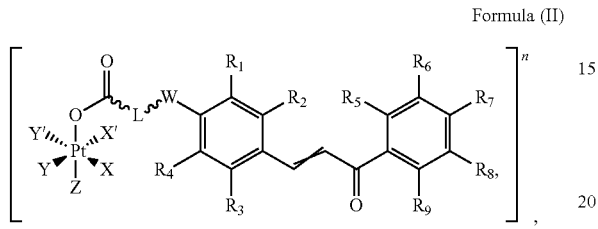

wherein X, X', Y, Y', Z, L, W, n and R$_1$ to R$_9$ are as defined in claim 1.

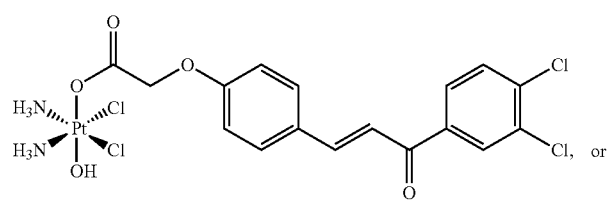

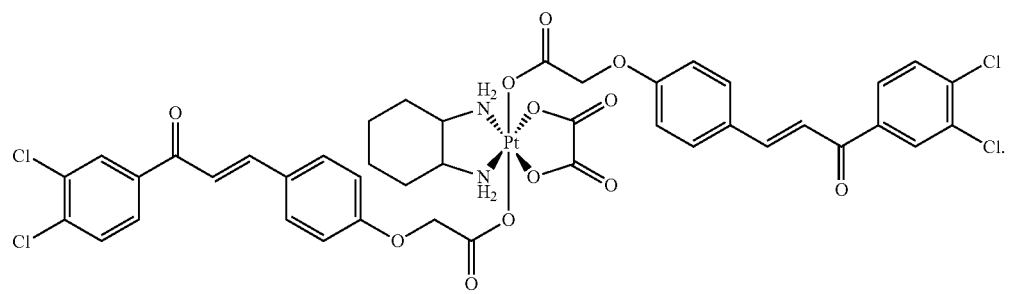

5. The platinum(IV) complex of claim 1, which comprises a structure of Formula (II):

Formula (II)

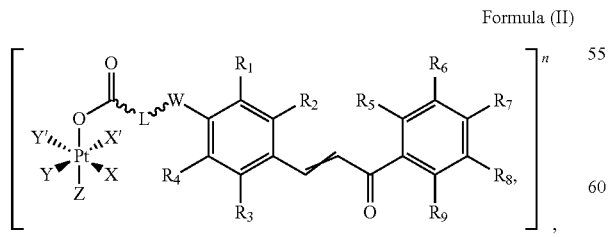

wherein:
X, X', Y and Y' are independently selected from ammine, oxalato, 1,2-cyclohexanediamine or a halido;

Z is selected from hydroxido or —OR with R being:

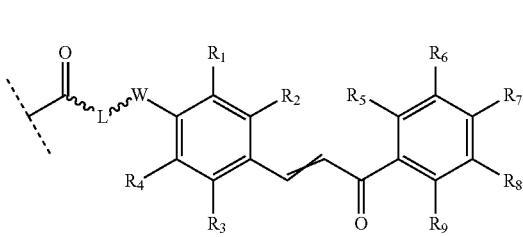

L is —(CH$_2$)$_m$— with m being an integer selected from 1, 2, 3 or 4;

W is selected from an oxygen atom or a sulfur atom;

R$_1$ to R$_9$ are independently selected from a hydrogen atom or a halogen atom.

6. The platinum(IV) complex of claim 5, which comprises a structure of Formula (IIa) or (IIb):

Formula (IIa)

Formula (IIb)

7. A method for preparing the platinum(IV) complex of claim 1 by linking a platinum(IV) complex precursor comprising a structure of Formula (XI):

Formula (XI)

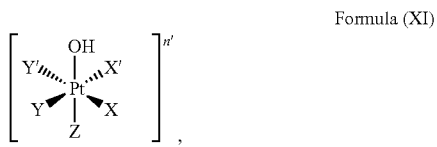

with an aryl-comprising moiety R to form the platinum complex of claim 1, wherein X, X', Y, Y' and Z are as defined in claim 1, n' means zero or any positive or negative charge and wherein the aryl-comprising moiety R is selected from one of:

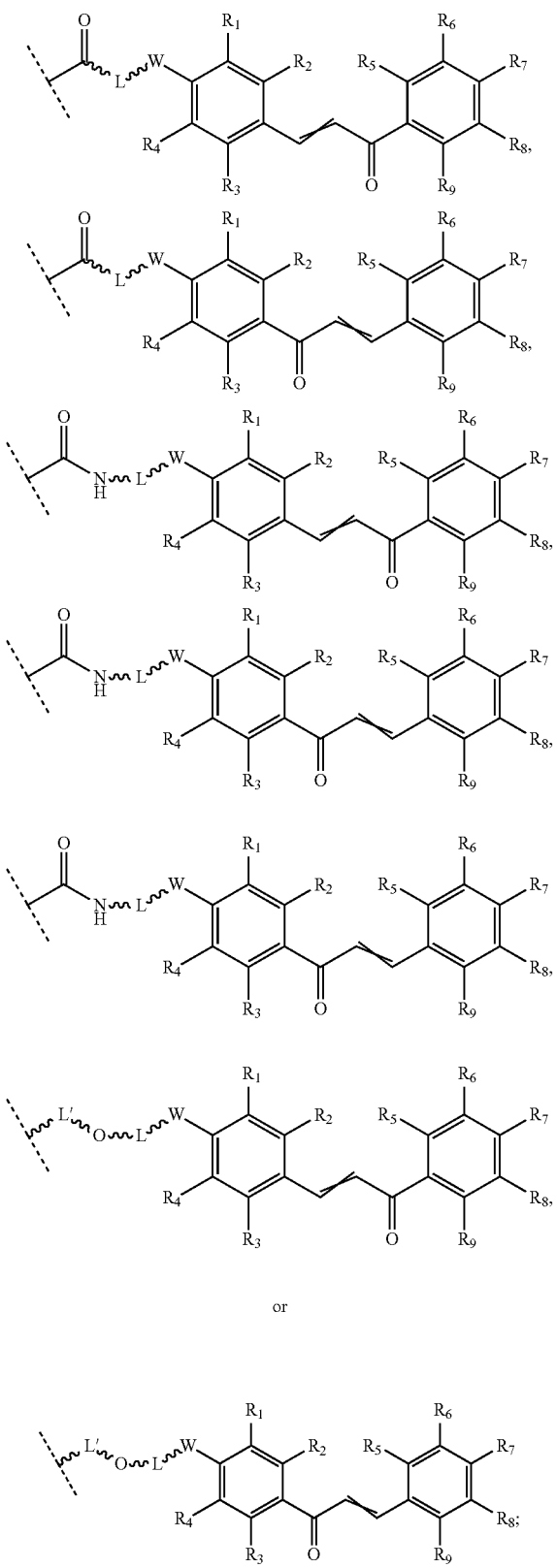

wherein L, L', W, and $R_1$ to $R_9$ are as defined in claim 1.

8. The method of claim 7 for preparing a platinum(IV) complex of the following Formula (II)

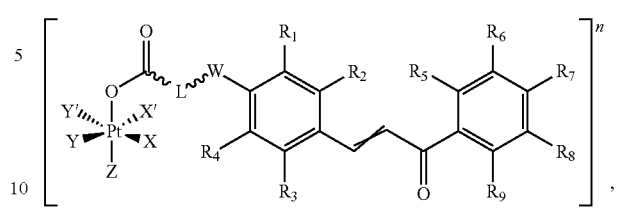

the method including linking a platinum(IV) complex precursor comprising a structure of Formula (XIa):

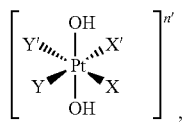

with X, X', Y, Y' and n' as defined in claim 1, with an aryl-comprising moiety which is

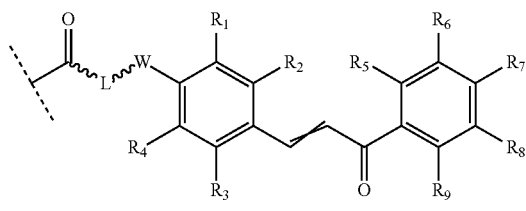

with L, W and $R_1$ to $R_9$ as defined in claim 1, which method comprises steps of:
(i) optionally preparing a hydroxysuccinimide(NHS)-ester of Formula (XII);

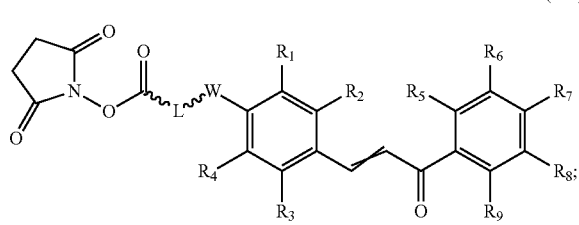

(ii) reacting a platinum(IV) complex precursor of Formula (XIa) with the N-hydroxysuccinimide(NHS)-ester of Formula (XII);
(iii) isolating the platinum(IV) complex of Formula (II).

9. A method for treating a subject suffering from a tumor or a cancer comprising administering an effective amount of a platinum(IV) complex of claim 1 to said subject.

10. The method of claim 9, wherein the method is for treating cancer selected from an ovarian cancer, a lung cancer, a breast cancer, or a colorectal cancer.

11. The method of claim 9, wherein the method is for treating cancer having an intrinsic or acquired cisplatin-resistance.

12. The method of claim 9, wherein the platinum(IV) complex comprises a structure of Formula (II):

Formula (II)

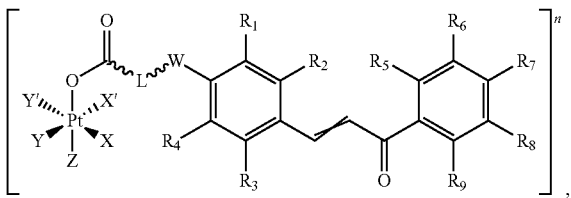

wherein X, X', Y, Y', Z, L, W, n and $R_1$ to $R_9$ are as defined in claim 1.

13. The method of claim 9, wherein the platinum(IV) complex comprises a structure of Formula (IIa):

Formula (IIa)

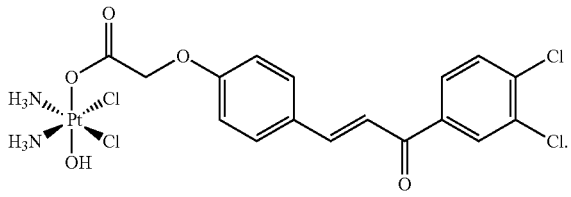

14. The method of claim 9, wherein the platinum(IV) complex is administered in form of a pharmaceutical composition comprising:

(i) the platinum(IV) complex; and (ii) a pharmaceutically tolerable excipient selected from a pharmaceutically tolerable carrier, salt, buffer, water, diluent, a filler, a binder, a disintegrant, a lubricant, a coloring agent, a surfactant or a preservative or a combination thereof.

15. A method of inhibiting the growth of tumor cells comprising the step of contacting a population of tumor cells with an effective amount of the platinum(IV) complex of claim 1.

16. The method of claim 15, wherein the tumor cells are cancer cells from one of an ovarian cancer, a lung cancer, a breast cancer, or a colorectal cancer.

17. The method of claim 15, wherein the tumor cells are cancer cells having an intrinsic or acquired cisplatin-resistance.

18. The method of claim 15, wherein the platinum(IV) complex comprises a structure of Formula (IIa):

Formula (IIa)

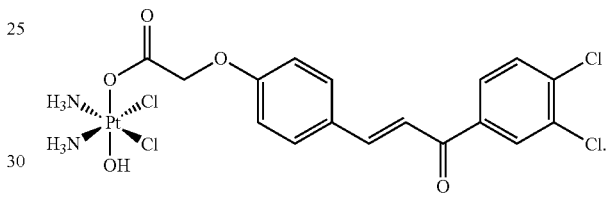

* * * * *